(12) United States Patent
Keränen et al.

(10) Patent No.: US 11,337,809 B2
(45) Date of Patent: May 24, 2022

(54) CARDIAC VALVE DOWNSIZING DEVICE AND METHOD

(71) Applicant: Medtentia International Ltd. Oy, Helsinki (FI)

(72) Inventors: Olli Keränen, Bjärred (SE); Per Antonsson, Malmö (SE)

(73) Assignee: Medtentia International Ltd Oy, Espoo (FI)

( * ) Notice: Subject to any disclaimer, the term of this patent is extended or adjusted under 35 U.S.C. 154(b) by 0 days.

(21) Appl. No.: 17/246,640

(22) Filed: May 1, 2021

(65) Prior Publication Data

US 2021/0259840 A1    Aug. 26, 2021

Related U.S. Application Data

(63) Continuation of application No. 17/169,456, filed on Feb. 6, 2021, which is a continuation of application
(Continued)

(30) Foreign Application Priority Data

Dec. 21, 2007 (EP) .................................. 07124048

(51) Int. Cl.
*A61F 2/24* (2006.01)
(52) U.S. Cl.
CPC .......... *A61F 2/2445* (2013.01); *A61F 2/2466* (2013.01); *A61F 2/2409* (2013.01);
(Continued)

(58) Field of Classification Search
CPC .... A61F 2/2445; A61F 2/2466; A61F 2/2448; A61F 2250/006; A61F 2/2457; A61F 2230/0091
See application file for complete search history.

(56) References Cited

U.S. PATENT DOCUMENTS 7,101,395 B2 * 9/2006 Tremulis ............ A61B 17/0401
623/2.11
7,261,868 B2    8/2007 Couvillon, Jr.
(Continued)

FOREIGN PATENT DOCUMENTS

WO    2006093656 A    9/2006
WO    2007030063 A    3/2007

OTHER PUBLICATIONS

WIPO, European International Search Authority, International Search Report dated May 11, 2009 in International Patent Application No. PCT/EP2008/068126, 4 pages.
(Continued)

*Primary Examiner* — Thomas McEvoy
(74) *Attorney, Agent, or Firm* — Tomas Friend

(57) ABSTRACT

A kit for repairing and/or replacing a mitral valve includes a mitral valve prosthesis and a loop-shaped element with a proximal end, a distal end, and a curved body. A proximal portion of the curved body is sized for positioning on an atrial side of the mitral valve and a distal portion of the curved body is sized for positioning on a ventricular side of the mitral valve. The distal portion has a first curved region with a radius of curvature that is larger than the radius of curvature of a second curved region so that the distal portion passes between heart muscle wall and chordae and circumflex the chordae of the mitral valve when the distal portion
(Continued)

is rotated into place at the ventricular side of the native mitral valve.

20 Claims, 18 Drawing Sheets

Related U.S. Application Data

No. 15/838,265, filed on Dec. 11, 2017, now abandoned, which is a continuation of application No. 12/808,174, filed as application No. PCT/EP2008/008126 on Dec. 20, 2008, now Pat. No. 9,867,702.

(60) Provisional application No. 61/016,331, filed on Dec. 21, 2007.

(52) U.S. Cl.
CPC .......... *A61F 2/2448* (2013.01); *A61F 2/2457* (2013.01); *A61F 2230/0091* (2013.01); *A61F 2250/006* (2013.01)

(56) References Cited

U.S. PATENT DOCUMENTS

| | | |
|---|---|---|
| 2003/0130730 A1 | 7/2003 | Cohn |
| 2004/0167620 A1 | 8/2004 | Ortiz |
| 2005/0149178 A1 | 7/2005 | Spence |
| 2006/0195134 A1 | 8/2006 | Crittenden |
| 2007/0208402 A1 | 9/2007 | Helland |

OTHER PUBLICATIONS

WIPO, European International Search Authority, Written Opinion dated May 11, 2009 in International Patent Application No. PCT/EP2008/068126, 6 pages.

WIPO, International Preliminary Examining Authority (European Patent Office), International Preliminary Report on Patentability dated Apr. 22, 2010 in International Patent Application No. PCT/EP2008/068126, 13 pages.

\* cited by examiner

FIG. 7
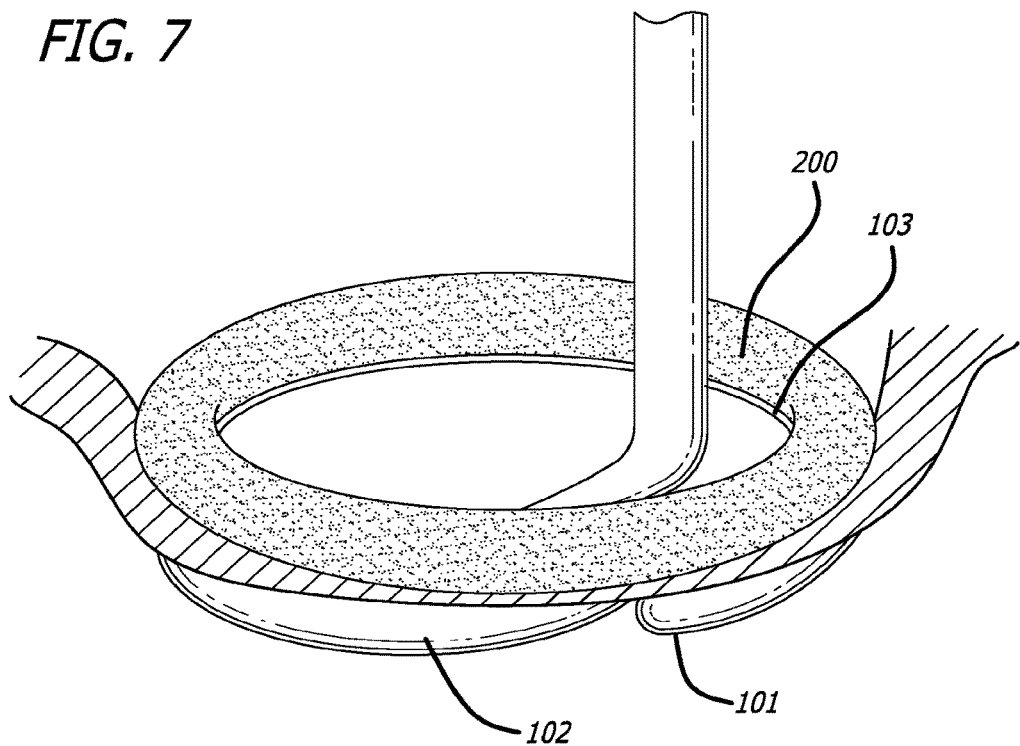
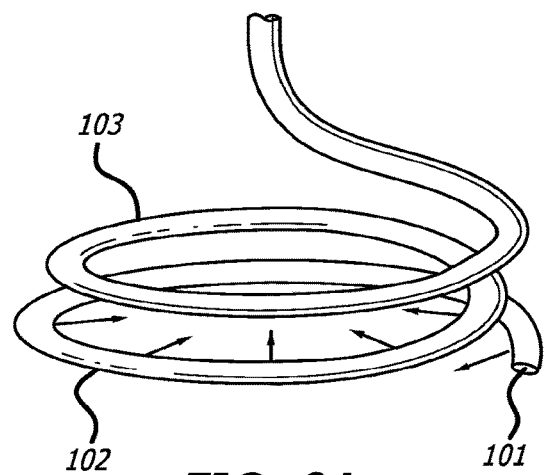
FIG. 8A
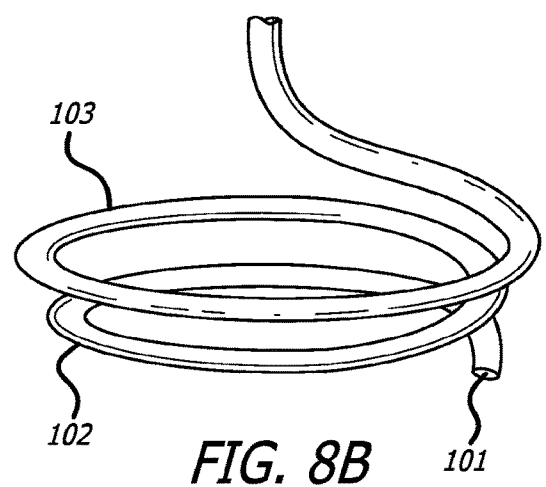
FIG. 8B

CARDIAC VALVE DOWNSIZING DEVICE AND METHOD

RELATED APPLICATIONS

This application is a continuation of and claims priority to U.S. patent application Ser. No. 17/169,456 filed Feb. 6, 2021, which is a continuation of U.S. patent application Ser. No. 15/838,265 filed Dec. 11, 2017, which is a continuation of Ser. No. 12/808,174 filed Sep. 13, 2010, which is the U.S. National Phase of and claims priority to International Patent Application No. PCT/EP2008/008126, International Filing Date Dec. 20, 2008, entitled Cardiac Valve Downsizing Device And Method, which claims benefit of and priority to U.S. Provisional Application Ser. No. 61/016,331 filed Dec. 21, 2007 entitled Pre-Annuloplasty Device And Method, and also claims priority to European Patent Application No. 07124048.5 filed Dec. 21, 2007 entitled Pre Annuloplasty Device And Method, all of which are hereby incorporated herein by reference in their entireties.

FIELD OF THE INVENTION

The present invention generally relates to heart valve repair and/or replacement techniques, annuloplasty devices, and related tools. More specifically, the invention relates to a medical device devised for facilitating or providing such heart valve repair techniques and/or heart valve replacement techniques for the repair of defective heart valves.

BACKGROUND OF THE INVENTION

Diseased mitral and tricuspid valves frequently need replacement or repair of various reasons. The mitral and tricuspid valve leaflets or supporting chordae may degenerate and weaken or the annulus may dilate leading to valve leak (valve insufficiency). The chordae tendinae, or heart strings, in short called the chordae, are cord-like tendons that connect the papillary muscles to the tricuspid valve and the mitral valve in the heart. The leaflets and chordae may become calcified and thickened rendering them stenotic (obstructing forward flow). Finally, the valve relies on insertion of the chordae inside the ventricle. If the ventricle changes in shape, the valve support may become non-functional and the valve may leak.

During heart valve replacement, sutures are spaced around the annulus (the point where the valve leaflet attaches to the heart) and then the sutures are attached to a prosthetic valve, see FIG. 3. The valve is lowered into position and when the sutures are tied, the valve is fastened to the annulus. The surgeon may remove all or part of the valve leaflets before inserting the prosthetic valve.

In heart valve repair, a defective valve is left in situ and surgical procedures are performed to restore its function. Mitral and tricuspid valve repair is traditionally performed with a suture technique, e.g. by performing the so-called Parachute procedure, see FIG. 2.

Heart valve repair and heart valve replacement may be performed in combination, e.g. a dilated leaflet may be partially surgically removed (e.g. leaving the chordae intact) and a heart valve replacement prosthetic valve may be affixed to the surgically modified anatomical heart valve in order to restore heart valve function.

Frequently an annuloplasty ring is used to fixate an altered size of the annulus and/or support the annulus. The annuloplasty ring serves to keep the annulus in a reduced diameter and to allow the existing leaflets to oppose each other normally again, in order to restore correct valve function. Sutures are used to attach the prosthetic annuloplasty ring to the annulus of the heart valve and to assist in plicating the annulus. Before permanently attaching the annuloplasty ring to the annulus, the latter is prepared to the desired shape by other means than the annuloplasty ring. This preparation of the valve in order to achieve a correct geometrical arrangement of the anatomical entities of a heart valve, and a restored correct function thereof, is hitherto performed manually by a surgeon. This part of the procedure is also called downsizing, which is explained in more detail below. Furthermore, manual downsizing may be dependent on a line of sight or suitable imaging modalities.

In addition, the form of the valve leaflets may be corrected by surgical techniques, e.g. tiny sutures, during the same surgical procedure. In general, the annuloplasty ring must be sutured to the valve annulus at the same time as a desired form of the latter is obtained at the end of the procedure. This simultaneous downsizing of the valve annulus and, which is time consuming and tedious. This means that two highly integrated processes are involved in the Parachute procedure, namely a) downsizing, perhaps including reshaping, of a dilated valve and b) a subsequent fixation of an annuloplasty ring. Thus, the Parachute procedure is highly dependent on the experience of the performing surgeon, who has to be able to think sterically, as it is necessary to firstly place the sutures on the annulus and then through the support ring.

A result of such a procedure may differ greatly and even provide a non-desired result, very much depending on the skills of the surgeon performing the procedure. If the ring is severely malpositioned, then the stitches must be removed and the ring repositioned relative to the valve annulus during restitching. In other cases, a less than optimum annuloplasty may be tolerated by the surgeon rather than lengthening the time of the surgery to restitch the ring.

During heart surgery, a premium is placed on reducing the amount of time used to replace or repair valves as the heart is frequently arrested and without perfusion. It would therefore be very useful to have a device and method to efficiently facilitate repair of heart valves or to facilitate attachment of a valve prosthesis into the mitral or tricuspid valve position.

There is a need of improving this downsizing. It would be advantageous to be less dependent on the human factor. Moreover, the surgeons would welcome a device and method facilitating this crucial operation.

In WO2006/054930, which is hereby incorporated by reference in its entirety for all purposes, a device for repairing a heart valve is disclosed that comprises an implantation instrument. The implantation instrument comprises a first support ring, and a second support ring connected to the first support ring to form a coiled configuration. The first support ring is configured to abut one side of the valve and the second support ring is configured to abut an opposite side of the valve to thereby trap a portion of the valve tissue there between. The device further comprises an annuloplasty implant adapted to be attached to the heart valve annulus in order to reshape the annulus and allow the leaflets to open and close properly. The annuloplasty implant is connected to the implantation instrument for insertion to the annulus. The implantation instrument disclosed in WO2006/054930 provides already a major improvement of the previously known devices and methods. However, the devices and methods as disclosed in WO2006/054930 may further be improved as a primary re-shaping for defining a working position of the insertion tool still has to be performed by the surgeon using a forceps instrument. Similar devices, suffering from analogous drawbacks are disclosed in e.g. US 2004/0167620, US 2005/0149178, and WO 2007/030063.

US2007/0038293 discloses methods, devices, and systems for performing endovascular repair of atrioventricular and other cardiac valves in the heart. Regurgitation of an atrioventricular valve, particularly a mitral valve, can be repaired by modifying a tissue structure selected from the valve leaflets, the valve annulus, the valve chordae, and the papillary muscles. These structures may be modified by suturing, stapling, snaring, or shortening, using interventional tools which are introduced to a heart chamber. The tissue structures can be temporarily modified prior to permanent modification. For example, opposed valve leaflets may be temporarily grasped and held into position prior to permanent attachment. However, the disclosure of US2007/0038293 does only provide local modification of certain portions of a heart valve, e.g. by grasping one or more leaflets for bringing these into a position suitable for fixation of a clip to the leaflets. Hence, the motion of the valve leaflets is only partly and temporary immobilized.

In WO 2006/093656 devices and methods are disclosed for aiding valve annuloplasty. The disclosed devices comprise a radiopaque deformable reference ring facilitating imaging based navigation of an annuloplasty procedure. However, the devices are not providing an active downsizing. Downsizing still has to be performed in a separate manner.

Therefore, there is a need to for devices and/or methods that further facilitate heart valve repair and/or replacement, e.g. by providing a suitable annuloplasty preparation of a cardiac valve area.

Thus, there is a need to provide a tool, medical device, or method that provides for a reliable and more easily accomplished valve repair or replacement. Facilitated, or less surgically demanding insertion of an annuloplasty implant and/or artificial heart valve would be advantageous. Hence, an improved tool, medical device or method would be advantageous and in particular a tool or method allowing for increased flexibility, user-friendliness, cost-effectiveness, and/or patient safety would be advantageous.

SUMMARY OF THE INVENTION

Accordingly, embodiments of the present invention preferably seek to mitigate, alleviate or eliminate one or more deficiencies, disadvantages or issues in the art, such as the above-identified, singly or in any combination by providing a medical device, kit and a method according to the appended independent patent claims.

In comparison with conventional annuloplasty, with the Parachute procedure, where the downsizing of a dilated valve and the reshaping as well as the fixation of the support ring are highly integrated into a tedious process, embodiments of the present invention provide for a separation (in time) of downsizing and reshaping. In particular, embodiments of the present invention provide for an advantageous downsizing, substantially simplifying the remainder of the valve repair or replacement procedure.

Embodiments, thus provide for both reducing complexity and time of previously known procedures.

Thus, according to a first aspect of the invention, a medical device is provided for repairing and/or replacing a heart valve comprised of valve tissue including an annulus and a plurality of leaflets for allowing and preventing blood flow through a patient's heart. The medical device is arranged for facilitating the repair and/or replacement of a defective heart valve of a heart of the and comprises a downsizing element devised to automatically provide downsizing of an annulus of the heart valve upon insertion of the downsizing element into the heart. The downsizing element is a loop shaped downsizing element devised to automatically provide downsizing of an annulus of the heart valve upon insertion of the downsizing element into the heart, wherein the downsizing element has a first shape to facilitate access to circumflex substantially all chordae of the heart valve, and a second shape to reposition the chordae towards a centre of the valve upon the insertion to provide the downsizing.

In some embodiments the downsizing element has a first shape to facilitate access to circumflex substantially all chordae of the heart valve, and a second shape to reposition the chordae towards a centre of the valve upon the insertion to provide the downsizing.

In some embodiments the medical device comprises a first loop shaped element configured to be positioned on a first side of an area of valve tissue oriented towards a cardiac chamber of the heart comprising a plurality of chordae, and wherein the first loop shaped element is arranged to at least temporary circumflex substantially all the chordae and to re-arrange a position of the chordae upon the insertion thereof to provide the downsizing.

In a second aspect a kit is provided for repairing a heart valve comprised of valve tissue including an annulus and a plurality of leaflets for allowing and preventing blood flow. The kit comprises a medical device for facilitating a repair and/or replacement of a defective heart valve of a heart of a patient according to the first aspect of the invention, wherein the device comprising a downsizing element devised to automatically provide downsizing of an annulus of the heart valve upon insertion of the downsizing element into the heart; and an annuloplasty implant adapted to be attached to the heart valve annulus in order to reshape the annulus and allow the leaflets to open and close properly, and/or a valve prosthesis adapted to be attached to the heart valve annulus or the annuloplasty implant in order to allow the heart valve to open and close properly.

According to a third aspect of the invention, a method is provided for repairing and/or replacing a heart valve comprised of valve tissue including an annulus and a plurality of leaflets for allowing and preventing blood flow. The method comprises inserting a medical device for automatically downsizing the annulus of the heart valve upon insertion of the medical device and prior to fixating an annuloplasty implant and/or valve prosthesis to the heart valve.

The invention contemplates various embodiments of the medical device, including embodiments for catheter-based surgery and embodiments for open heart surgery.

According to a second aspect of the invention, a method is provided, comprising using the medical device according the first aspect of the invention in a medical procedure for repairing a heart valve comprised of valve tissue including an annulus and a plurality of leaflets for allowing and preventing blood flow through a patient's heart.

Some embodiments provide for advantageous devices and/or methods for facilitating and/or providing treatment of regurgitation of mitral and tricuspid valves.

Further embodiments of the invention are defined in the dependent claims, wherein features for the second and subsequent aspects of the invention are as for the first aspect mutatis mutandis.

Various additional objectives, advantages and features of the invention will become more readily apparent to those of ordinary skill in the art upon review of the detailed description of the illustrative embodiments.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which

FIG. 7 is a schematic view of the medical device of FIGS. 6a-6c with an annuloplasty prosthesis attached thereto, in use at a heart valve tissue;

FIGS. 8a and 8b are schematic views of an embodiment of the medical device of FIG. 7 having a change of shape during use;

DESCRIPTION OF EMBODIMENTS

Figure 1A:
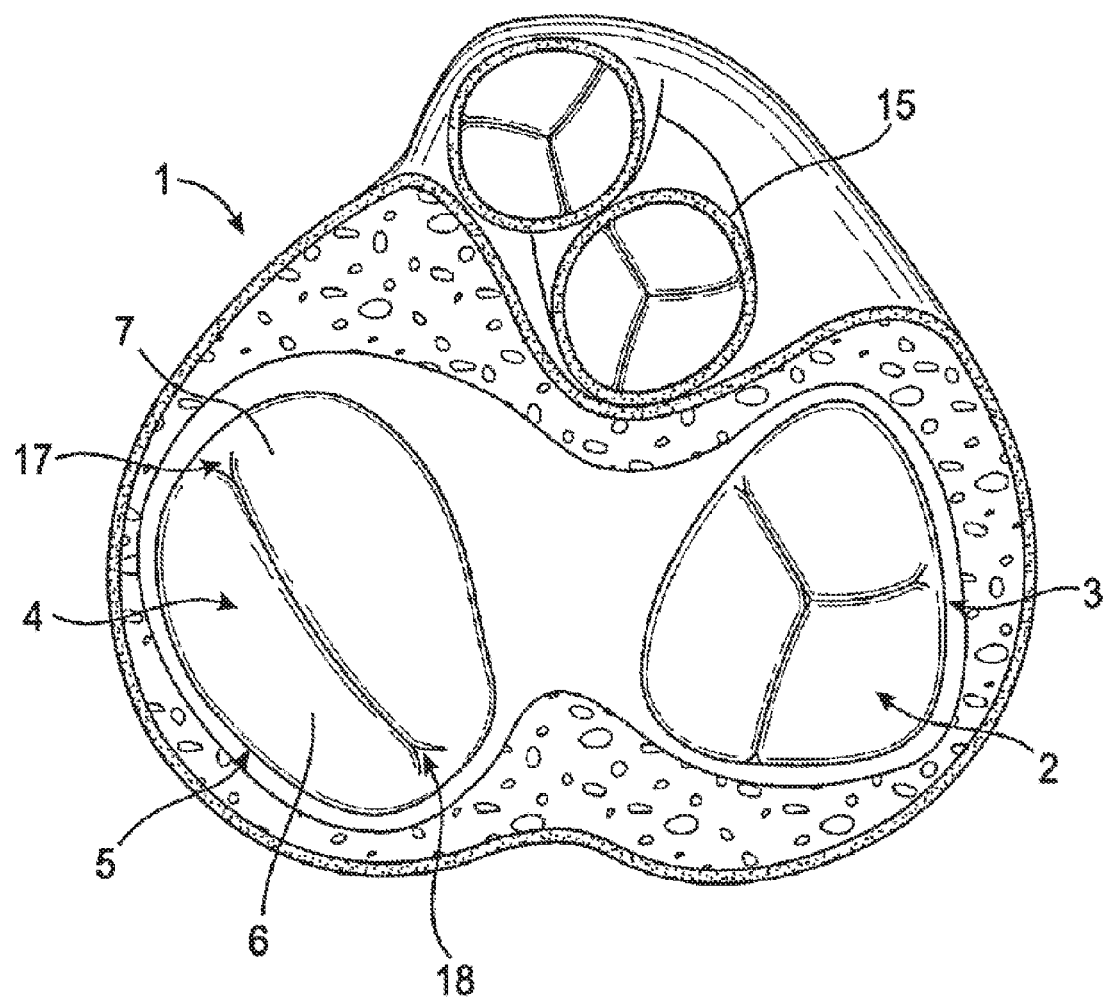
FIG. 1a is a schematic cross-sectional view of a heart showing the arrangement of the heart valves.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The following description focuses on an embodiment of the present invention applicable to a repair of a defective heart valve and in particular to a reshaping the valve shape and/or area in order to facilitate insertion of an annuloplasty implant and/or artificial heart valve. However, it will be appreciated that the invention is not limited to this application but may be applied to many other heart valve disorders for which downsizing and/or reshaping of the valve shape and/or area is needed. For instance, a heavily dilated heart valve may be replaced with a heart valve prosthesis, wherein existing anatomical structures may be removed or partly removed. For instance, a part of the valve leaflets may be surgically removed, wherein it may be desired to keep as much of the leaflets as possible, e.g. without having to cut off the chordae. An anatomically correct size of the heart valve prosthesis is preferably chosen for providing a restoration of valve function, which may necessitates downsizing, i.e. reshaping the dilated valve shape and/or area, prior to fixating the heart valve prosthesis. This downsizing is provideable by embodiments of the present invention.

The methods and devices are applicable for both downsizing of mitral and tricuspid valves.

Figure 2:
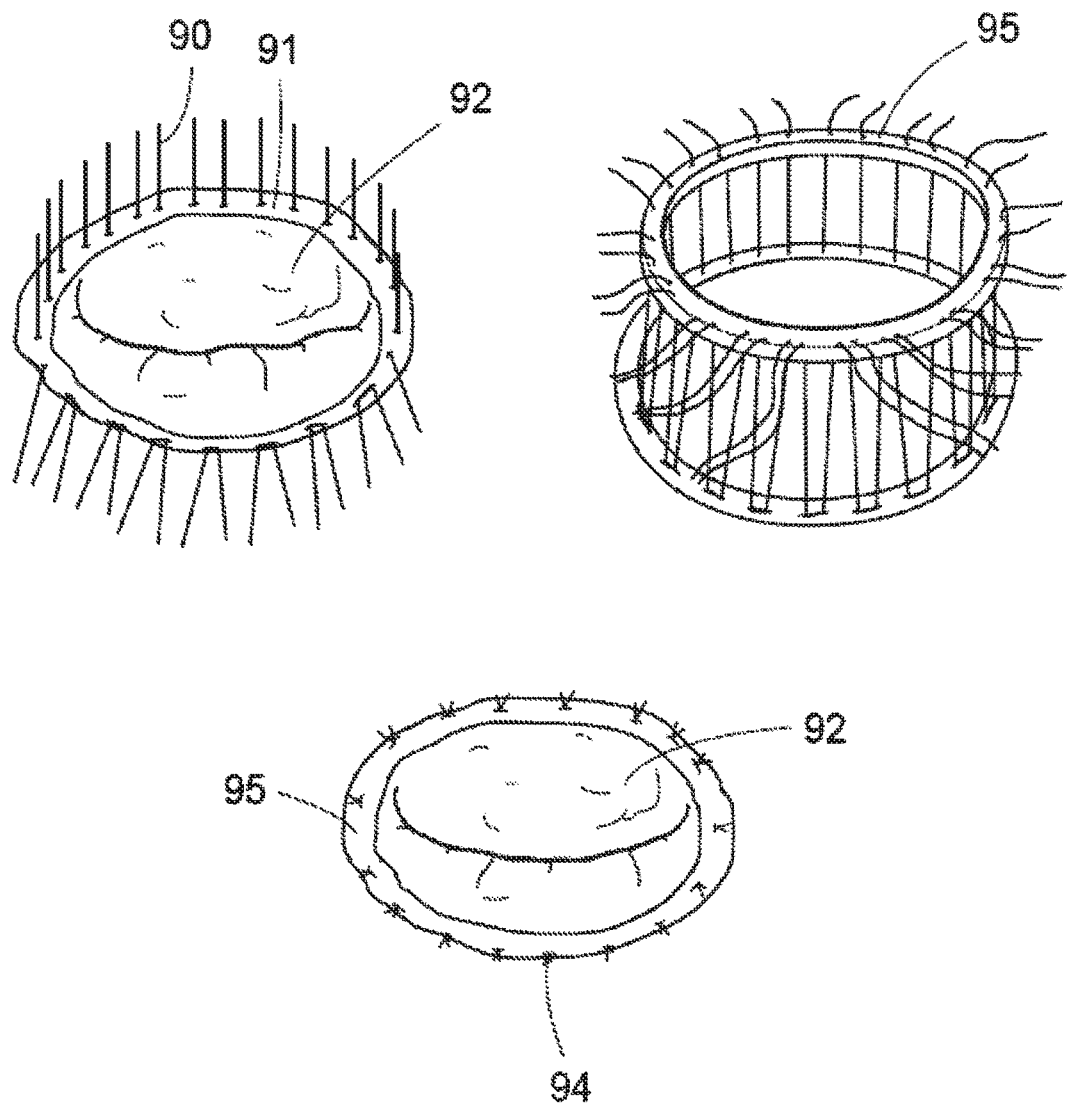
FIG. 2 are perspective views illustrating the positioning of an annuloplasty ring by using the Parachute technique.
Figure 3:
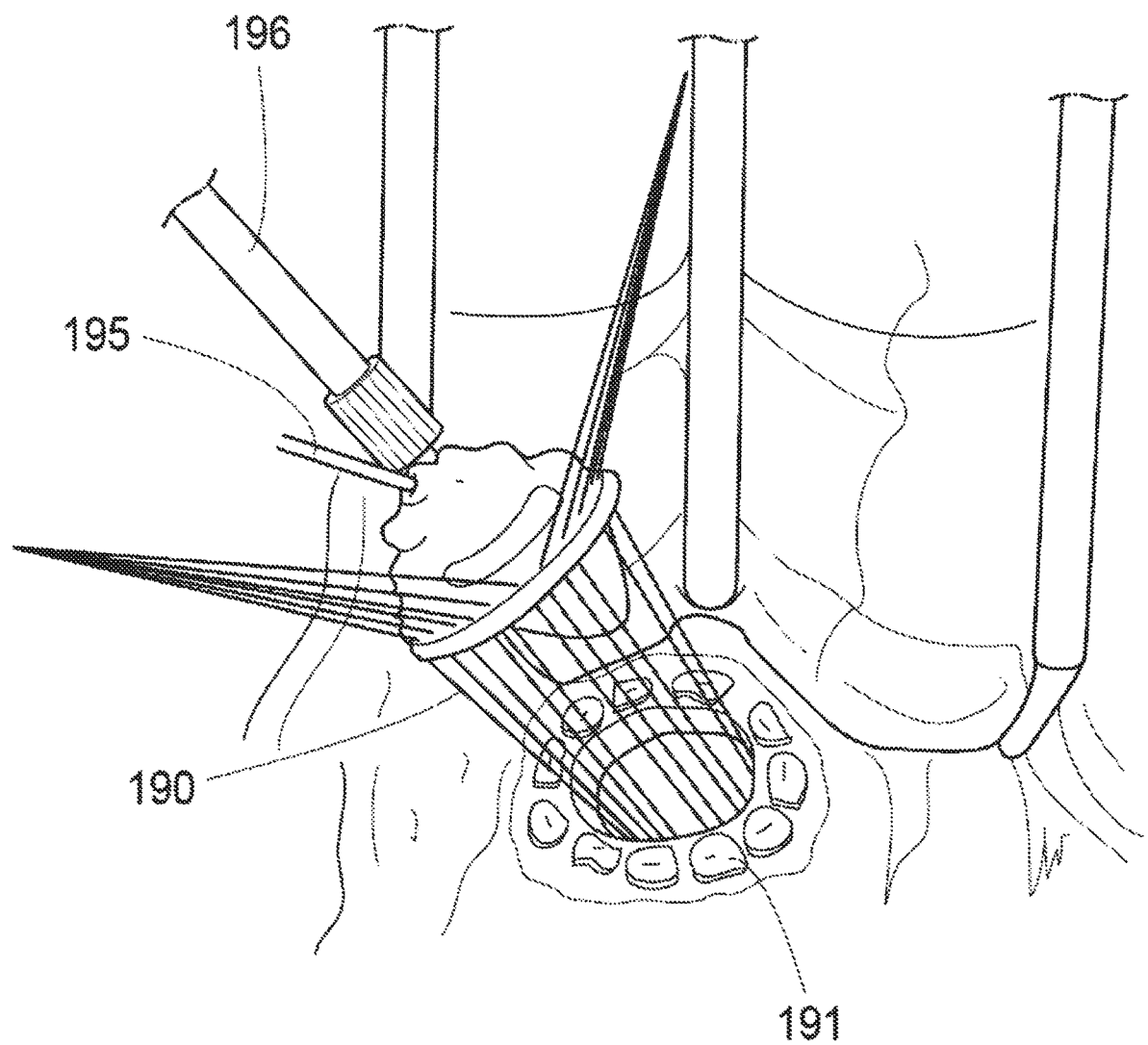
FIG. 3 is a perspective view illustrating the positioning of a valve prosthesis by using the Parachute technique.

In conventional annuloplasty surgery a leaking valve, e.g. mitral valve, is adapted to a smaller diameter by means of a supporting ring, with a smaller diameter and/or area than the diameter and/or area of the leaking valve, and is fixated at a correct position by means of sutures (commonly by applying the tedious Parachute procedure illustrated in FIGS. 2 and 3). As mentioned above, the Parachute procedure, sets demands on the performing surgeon, who has to be able to think sterically, as it is necessary to firstly place the sutures on the annulus and then through the support ring. The chance of failure is great. Furthermore, with the Parachute procedure, the downsizing of a dilated valve and the fixation of the support ring is a highly integrated process. An improvement provided by some embodiments of the present invention might be described as a separation (in time) of these two events; downsizing, and fixation. Thus, embodiments provide for reducing both complexity and time for the combined procedure.

The term "downsizing" as used in the present specification is to be understood as an alteration of a heart valve, e.g. for a pre-annuloplasty, by means of 1) changing the shape or contour described by the heart valve annulus, or
2) changing (i.e. reducing) the area described by the annulus, or
3) both 1) and 2).

These changes might be in a two dimensional plane or in a three dimensional plane.

A successful downsizing may be appraised by the leaflets of a heart valve having regained proper coaptation. Hence, some embodiments of the invention provide a restored proper coaptation of heart valve leaflets. This may be permanently fixated by annuloplasty implants subsequently fixated to the annulus of the heart valve. In addition, or alternatively, some embodiments of the invention provide a permanent downsizing and are left in place in the body. In addition, or alternatively, some embodiments of the invention may provide an improved, restored or proper leaflet coaptation that in addition is permanently supported by an artificial heart valve, in order to provide proper heart valve function.

The aspect of downsizing, as defined above, may be performed in many ways. Some may be more suitable at specific circumstances although not applicable in others. Within the interior of the heart some anatomical structures may be pushed, pulled or stretched to enforce a reshaping of an adjacent valve, i.e. the chordae, the leaflet or the annulus may be manipulated accordingly to achieve the desired downsizing of the heart valve. When the desired downsizing is achieved, the heart valve may be permanently fixated in this shape and/or area by suitable elements, such as annuloplasty devices, or by leaving a downsizing element permanently in its position.

"Heart valve repair" as used in this specification may include heart valve replacement. Heart valve repair may comprise installation of artificial heart valve prosthesis. For instance, a dilated heart valve leaflet may be partially surgically removed (e.g. leaving the chordae intact) and a heart valve replacement prosthetic valve may be affixed to the surgically modified anatomical heart valve in order to restore heart valve function. Also, an artificial heart valve prosthesis may be attached to an annuloplasty device. Downsizing is thus alternatively or in addition to fixation of annuloplasty devices provided prior to fixation of artificial heart valves. Some embodiment provide for advantageous heart valve repair, as e.g. described with reference to FIGS. 18 and 19.

Figure 1B:
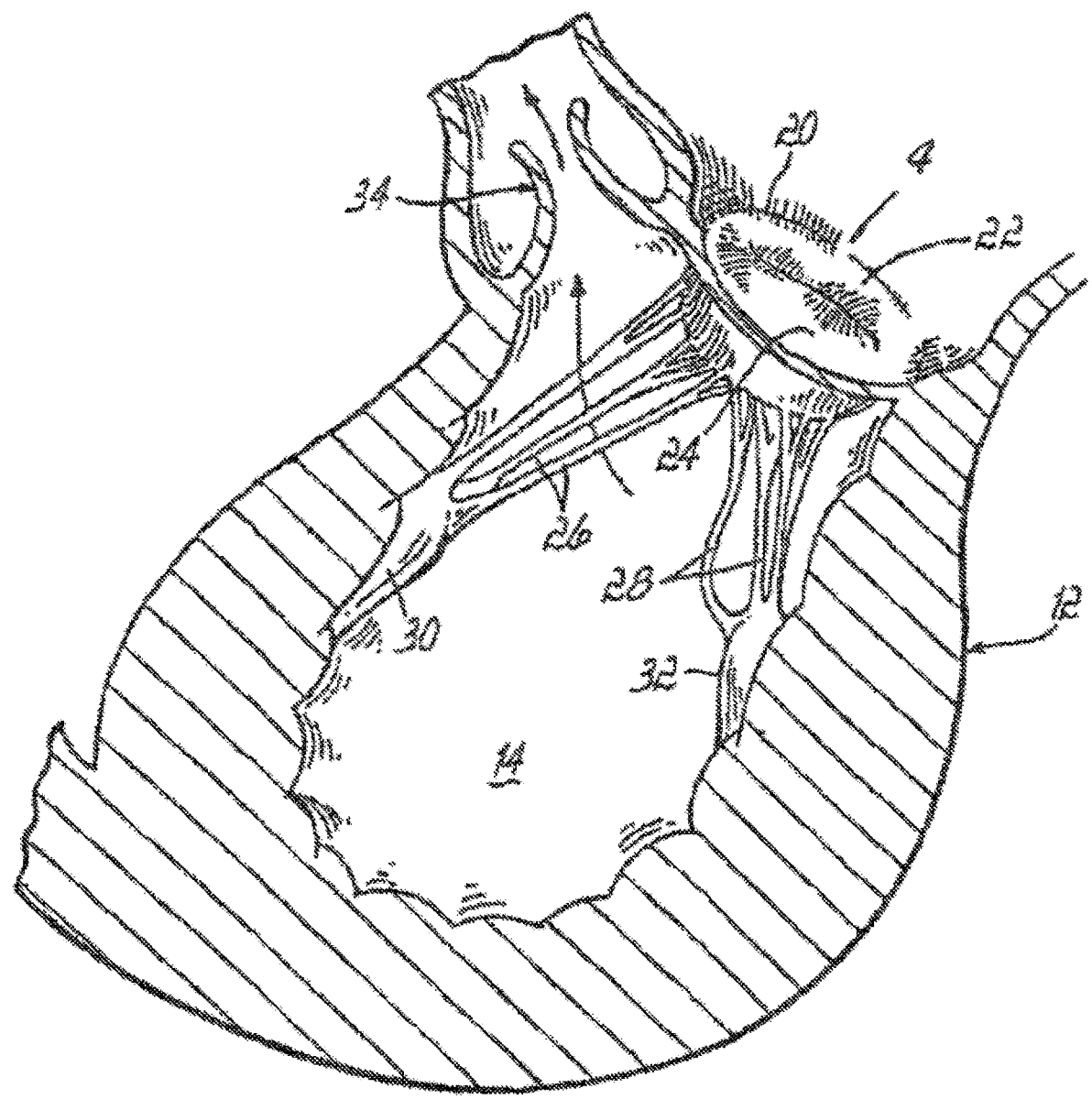
FIG. 1b is a cross sectional view of the left ventricle showing a mitral valve in perspective.

FIGS. 1a and 1b are given for illustrating the anatomical situation where embodiments of the invention are implementable. FIG. 1a is a schematic cross-sectional view of a heart 1 having a tricuspid valve 2 and tricuspid valve annulus 3. The mitral valve 4 is shown adjacent a mitral valve annulus 5. The mitral valve 4 is a bicuspid valve having an anterior cusp 7 and a posterior cusp 6. The anterior cusp 7 and the posterior cusp 6 are often referred to, respectively, as the anterior and posterior leaflets. FIG. 1a also shows the aorta 15, which is located adjacent the wall of the left atrium on the anterior side of the mitral valve. Also shown in the figure are the posterior commissure 17 and the anterior commissure 18. FIG. 1b is a cross sectional view of the left ventricle showing the mitral valve 4 in perspective. FIG. 1b illustrates a patient 10 having a heart 12 shown in cross section including a left ventricle 14. The concepts of the present invention are suitable to be applied, for example, to a mitral valve 18 which supplies blood into left ventricle 14. Mitral valve 18, as better shown in FIG. 1a, includes an annulus 20 and a pair of leaflets 22, 24 which selectively allow and prevent blood flow into left ventricle 14. It will be appreciated that the term annulus tissue is used extensively throughout this disclosure in reference to the drawings, however, the inventive principles are equally applicable when referring to other valve tissue such as leaflet tissue or other attached vessel tissue. Leaflets 22, 24 are supported for coaptation by chordae tendinae or chords 26, 28 extending upwardly from respective papillary muscles 30, 32. Blood enters the left ventricle 14 through the mitral valve 4 and is expelled during subsequent contraction of the heart 12 through the aortic valve 34. It will be appreciated that the present invention is applicable to tricuspidal heart valves as well.

Downsizing methods and devices will now be described in more detail.

A) Collecting Chordae

In embodiments, a medical devices collects the chordae, or bundles of chordae, for providing a downsizing of the corresponding adjoining heart valve. Some embodiments collect at least substantially all the entire chordae in a single working operation.

In more detail, the medical devices comprise a downsizing element devised to automatically provide downsizing of an annulus of the heart valve upon insertion of the downsizing element into the heart. Insertion may be performed from the atrial side or the ventricular side of the valve.

In some embodiments the downsizing element is arranged to automatically reposition the chordae 26, 28, e.g. towards a centre of the valve, upon the insertion to provide the automatic downsizing. Thus the medical device facilitates a repair and/or replacement of a defective heart valve of the heart of a patient.

Specific embodiments of chordae manipulating downsizing elements will now be described.

Helical Devices

In some embodiments, which are elucidated in more detail below, medical devices are provided that are arranged and comprise at least one downsizing element to physically circumflex around substantially the entire chordae tendinae of a valve, gripping the latter in a gentle manner such that a distinct temporary downsizing of the valve is automatically provided by inserting the medical device accordingly.

In some embodiments the downsizing element has a first shape to facilitate access to circumflex substantially all chordae 26, 28 of the heart valve, and a second shape to reposition the chordae 26, 28 towards a centre of the valve upon the insertion to provide the downsizing.

In embodiments the downsizing element comprises a first loop shaped element configured to be positioned on a first side of an area of valve tissue oriented towards a cardiac chamber of the heart comprising a plurality of chordae. The first loop shaped element is arranged to at least temporary circumflex substantially all the chordae 26, 28 and to re-arrange a position of the chordae 26, 28 upon the insertion thereof to provide the downsizing. The first loop shaped element is brought into apposition with the chordae and then draws together the chordae in a suitable manner. This may be provided by reducing the interior area or shape, e.g. the diameter, of the first loop shaped element in relation to the anatomical diameter of the chordae. Reducing the area or shape may be provided actively, e.g. by shape memory materials, tendons etc., as described below. Alternatively, or in addition, the reduction area or shape may be provided in a more passive way, e.g. by rotating a first loop shaped element, having a decreasing inner area or shape in axial direction thereof, axially along the chordae.

In a superior view of the heart the valves are blocking the view of the chordae tendinae, as shown in FIG. 1a. However, the anatomy of the valve makes it possible to go beneath a valve, e.g. through a commissure thereof or by penetrating the annulus thereof, and thereby reaching an anatomical space near the valve between the wall of the heart and the chordae tendinae. Thus, the chordae may be collected within a helical device comprising the first loop shaped element, whereby the chordae may be drawn together for downsizing the valve, upon insertion of the device. Downsizing is thus provided by making use of the helix-shaped device.

In an embodiment the helical device has a helical structure that is arranged o cylinder and where a defined distance is kept between subsequent turns of the helix, i.e. a hollow centre and a free space is provided between each turn.

In some embodiments the helix comprises only a single turn arranged to be introduced to the cardiac chamber side of the valve.

The helix may have a blunt tip in order to not harm the anatomical structure of the heart. The tip of the device may be arranged with a larger diameter than the subsequent part of the helix that circumflexes the chordae.

The device may be inserted through either commissure at a valve or penetrating through the valve annulus, whereby the chordae tendinae will be circumflexed by the helical structure as the device is inserted continuously. The diameter of the helical structure, i.e. diameter of the imaginary cylinder, is defined prior to insertion and may be set smaller than corresponding value of the valve, hence the valve will be downsized as the helix is inserted and circumflexing all of the chordae tendinae.

In more detail, the helical device comprises the first loop shaped element, which thus is "loop-shaped" with an open distal end. The loop shape is provided as a curved shape that is continuous towards a proximal part of the device, e.g. with a circular, elliptic, or D-shaped form or any other curvature which may provide a suitable downsizing of the shape of the valve annulus. The term "loop-shaped" also includes a curved shape that is open forming an arcuate shape, such as a C-shape or U-shape. The term "loop-shaped" also includes a curved shape overlapping itself to form a portion of a coil. The term "loop-shaped" also includes three dimensional curves as mentioned in the previous paragraph. The number of loops of the helix may be different and vary from e.g. a half turn (e.g. C-shape or U-shape) up to several turns.

The cross section of the helix may differ along the longitudinal extension of the helix in some embodiments.

Some embodiments may be provided for catheter-based surgery, for transvascularly introducing into position. Some embodiments may be provided for open heart surgery, e.g. in a rigid configuration.

Several loop shaped embodiments are described in more detail below with reference to FIGS. 5a to 19.

Catheter, Wire, Core, Sheath or Sleeve

A catheter and/or wire may be fed generally axially into place around the entire, or at least substantially the entire chordae (either through the leaflets from the atrial chamber or from the ventricular side of the valve).

In the case of using the catheter, e.g. a wire is fed into the central lumen to form the catheter to the desired curvature around the chordae, gather the chordae, and alter the curvature of the valve annulus, generally to a smaller diameter or radius through at least a segment of the annulus circumference. The wire may for instance be pre-shaped, spring formed, memory biased, tension wound or braided, plastic polymer formed, in order to achieve the desired curvature.

A wire of pre-formed shape may also be provided and used to change the shape of the catheter upon axial rotation of the wire after it has been fed into the catheter.

In another embodiment, the catheter may also be altered in shape or curvature as a result of fluid (gas or liquid) pressure or vacuum exerted on the inner lumen of the catheter, as in the case of a balloon catheter. In this case, the catheter may be provided as shape biased to curve under pressure applied to the central lumen or when pressure or vacuum is applied to one of a plurality of lumen, creating a high pressure distended lumen and/or a low pressure contracted lumen, as desired, in order to circumflex, grab and modify an anatomical structure, such as the entire chordae of a heart valve.

In the case of the wire initially placed as a guide around the chordae, a sleeve or catheter of a desired curvature may be fed over the wire and around the chordae to gather the chordae and alter the curvature of the valve annulus, generally to a smaller diameter or radius through at least a segment of the annulus circumference. The catheter may for instance be pre-shaped, spring formed, memory biased, tension wound or braided, plastic polymer formed, in order to achieve the desired curvature.

A sleeve or catheter of pre-formed shape may also be used to change the shape of the catheter upon axial rotation of the sleeve or catheter after it has been pushed over the wire.

Steerable Guide or Catheter

Figure 17:
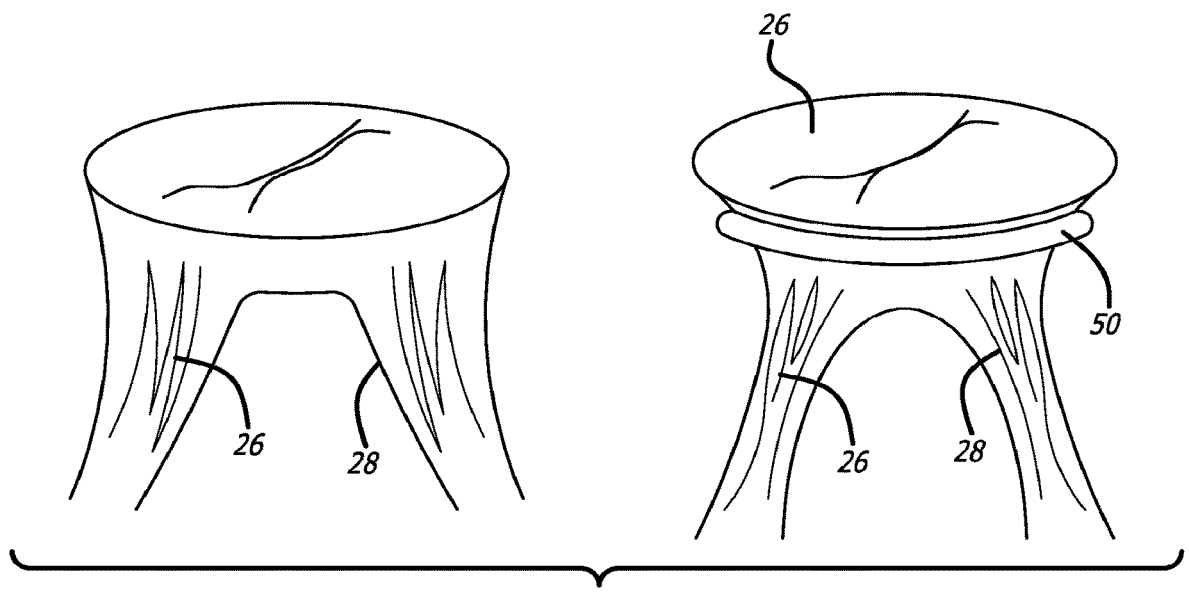
FIG. 17 is schematic illustration of another device providing pre-annuloplasty downsizing.

In addition to pre-shaped wires, catheters or sleeves, actively steerable wires or catheters may be provided and used to modify an anatomical cardiac structure for achieving a downsizing. For instance, in case the annulus does not have a smooth path, abrupt change in direction or is extensively elongated or presents some other irregularity, a steerable device may be provided. As the path may be blocked, while inserting the device through a commissure, small adjustments of e.g. the direction of the tip of the device may steer and overcome the obstacle. Insertion of a helical device via either commissure and rotating the device, e.g. a full loop, i.e. a 360 degree turn, parts thereof, or multiples thereof, introduces the device in the interspace between the heart muscle wall and the chordae tendinae. Thus the entire, or at least substantially the entire chordae tendinae are circumflexed by the device, as e.g. illustrated on the right in FIG. 17 showing a medical device 50 circumflexing the chordae and downsizing a heart valve annulus.

After this initial procedure the actual retraction of the chordae tendinae towards the centre of the annulus may be already be achieved by the shape of the medical device. Alternatively, or in addition, the retraction of the chordae may be provided by an electroactive system implemented within the device. Intrinsic parts of the device may be activated by electric energy. The total length of the device may be shortened in this manner, and hence its circumference gets smaller, resulting in a downsizing of the annulus. The device may be configured to be elongated on its outer while it is shortened on the inside or only one of these configurations. The effect is that the device will get a curvature, bending in the direction of the device gets shorter.

a) Tendons

Tendons or tension elements may be used in an inner lumen of a catheter structure to generate a compressive force on one side of a catheter wall in order to provide a controllable curvature of the catheter. Tension in the tendon is for instance generated by a screw or pully mechanism, remotely operated e.g. in the catheter handle. The curvature of the distal catheter tip is determined by the form of the catheter wall itself, e.g. its wall thickness, notches or features to allow flexibility in the catheter. In U.S. Pat. No. 6,976,987, which is hereby incorporated by reference in its entirety for all purposes, a dual profile steerable catheter is disclosed, which is used for treating e.g. cardiac arrhythmia. The catheter has tendons housed within a sheath such that a movement of tendons in proximal direction causes a distal end region of the sheath to deflect.

However, such a steerable catheter has hitherto not been provided or used for downsizing purposes. A steerable catheter may be fed generally axially into place a the chordae, either through the leaflets from the atrial chamber or from the ventricular side of the valve, and the shape of the catheter may be altered, e.g. using tendons, to form the catheter to the desired curvature around the chordae, gather the chordae, and thus alter the curvature of the valve annulus, generally to a smaller diameter or radius through at least a segment of the annulus circumference.

In a similar sense, elements may be provided and used to create a pushing force, instead of a pull, in a catheter lumen to deflect the catheter or a downsizing element of the medical device.

b) Electroactive Polymers, I.e. Micromuscles

The shape of the medical downsizing device may be actively controlled, e.g. by electroactive polymers. Electroactive polymers are known to increase or decrease in bulk volume, which may be used to create expansion or contraction forces on one side or another of a catheter lumen.

In U.S. Pat. No. 7,261,686, which is hereby incorporated by reference in its entirety for all purposes, an universal, programmable guide catheter for coronary treatment is disclosed, which comprises electroactive polymer actuators to change shape of the catheter based on control signals received from a control unit. In U.S. Pat. No. 7,128,707, which is hereby incorporated by reference in its entirety for all purposes, electroactive polymer based artificial sphincters and artificial muscle patches are disclosed for treating, e.g. fecal incontinence, which has a cuff for placement around a body lumen and electroactive polymer actuator. A control unit is provided for controlling the actuators to expand or contract the cuff. The artificial muscle patches, which are adapted to be implanted adjacent a patient's heart, and the artificial sphincter cuffs are adapted to be implanted around a body lumen, such as the urethra, the anal canal, or the lower esophagus.

However, such electroactive polymer actuators have hitherto not been provided or used for downsizing purposes. A construction comprising electroactive polymer actuators may for instance be provided at a catheter tip or distal portion of a partly flexible helical downsizing device, allowing for gathering anatomical structures like the chordae and downsizing of a heart valve annulus.

Rotating Elements

Rotating elements may be used for changing the curvature of downsizing elements. For instance the above mentioned wire may comprise sections of elements rotatable relative each other with an inclination angle, thus leading to a curvature of the wire controllable by rotating the latter, e.g. in relation to a distal end of the wire fixed to a catheter sheath. The downsizing element may be introduced through a commissure and be guided in between the wall of the heart and the chordae tendinae. As a full 360 degree rotation is completed the outer most end of the inserted device returns to the commissure and site of entrance.

Steered Lasso

The thread tip may be pulled as a lasso structure, whereby gently applying a pulling force to the ends of the thread will downsize the valve in respect to the amount of force applied.

B) Pulling Leaflets

Forceps

The alteration of a valve may be provided by pulling the outer rim of the leaflet by means of a forceps device. The reduction in size of the valve depends on the applied force, on each leaflet, and on the overall rigidity of the anatomic structures of the heart surrounding the specific valve in question. The valve may be altered to a larger extent in the transversal than in the longitudinal direction by the method; however it will depend on how the applied force is distributed across the annulus. For instance, using at least one forceps for each leaflet to grab gently the edge of each leaflet and pulling the edges towards each other, the size of the valve may be altered. This downsizing using forceps may be performed automatically, e.g. robot based and/or ultrasound feedback controlled.

Adjustable Tapes Pulling the Annulus

Another approach is to apply an adjustable tape pulling the annulus. With an adhesive surface a strip may be attached to the leaflets, thus securing a firm grip, whereby the leaflets may be pulled toward each other. The adhesive must be designed for biological tissue to have a desired effect of firmly attach to the leaflet. By using more positions where the force is applied for each leaflet, the pulling force may be more evenly distributed across the leaflet base, whereby the valve is smoothly reshaped, and a downsized valve results. This downsizing using adjustable tapes may be performed automatically, e.g. robot based and/or ultrasound feedback controlled.

Attach Arms to Annulus

Another method may comprise attaching arms to the annulus, i.e. distal the leaflet edge, and applying a pulling force with these arms. Thus the size and/or area of the valve may be altered. The arms may have barbs or an adhesive surface at the outer end securing a firm grip at the annulus. The effect is dependent on how firmly the arms are anchored at the annulus and the numbers of arms, the amount of force applied and the overall rigidity of the heart surrounding the annulus. This downsizing using arms may be performed automatically, e.g. robot based and/or ultrasound feedback controlled.

Alfieri Type of Method Temporarily on Leaflet Edges

An "Alfieri" type repair for mitral insufficiency may be performed by suturing the free edges of the leaflets together thus generating a double orifice appearance. The procedure is performed by open heart surgery and may be suitable in downsizing a valve temporarily.

Percutaneously similar results are found by using Mitraclip (Evalve Inc., Redwood City, Calif., US). The device, a fabric covered clip capturing both free edges of the leaflets, is delivered by a transseptal catheter creating a double orifice. However, the valve annulus has hitherto not been modified or downsized when using the Mitraclip devices. Furthermore, the Mitraclip devices did hitherto not allow for an automatic pre-annuloplasty change of shape of the annulus for facilitating the annuloplasty procedure.

Additional methods are available using the Mobius device (Edwards Lifesciences, Irvine, Calif., US) which captures the free leaflets via a transatrial guide catheter. The process uses a vacuum port to secure the leaflet and a needle places a suture. The process is then repeated for the adjacent leaflet. As both leaflets are captured they are drawn together and a small clip securing the suture finishes the procedure. However, also the Mobius device has hitherto not been used for downsizing.

C) Encircling Collar

Encircling collars may be provided for downsizing purposes, e.g. in form of lassos, clamps or cuff collars, as explained below.

Lasso

A lasso may be placed around the valve chordae, either through the leaflets from the atrial chamber or from the ventricular side of the valve. The chordae may then be gathered, and the curvature of the valve annulus altered, generally to a smaller diameter or radius through at least a segment of the annulus circumference, i.e. a downsizing is achieved. An automatic downsizing to a desired degree of downsizing may be achieved by providing a suitable end position or stop of the lasso.

In U.S. Pat. No. 7,297,144, which is hereby incorporated by reference in its entirety for all purposes, methods for electrically isolating a portion of the atria are disclosed. In particular, drawing items 140 & 142 on cover page or sheet 13 describe a lasso.

In U.S. Pat. No. 6,123,703, which is hereby incorporated by reference in its entirety for all purposes, an ablation catheter and methods for treating tissues are disclosed. In particular on drawing sheet 7 or 8 of U.S. Pat. No. 6,123,703 a deployable closed loop is shown. However, U.S. Pat. No. 6,123,703 deals with an ablation catheter system for treating tissues or atherosclerotic tissues of a patient. The catheter system has a retractable metallic element means comprising the deployable close loop with a running noose at its end, and the ablation catheter provides RF therapy to the tissues through the retractable metallic elements means.

However, such a lasso or closed loop has hitherto not been provided or used for downsizing purposes.

Clamp

A clamping device may be positioned around the external features of the heart, e.g. around the atrial-ventricular (AV) groove or on the left ventricular free wall to push in the valve annulus anatomy and bring the annulus into the desired shape for placement or a prosthetic device. The clamp may be in the form of at least one and perhaps two opposed clamping surfaces. The clamp may have a shape to match the desired heart anatomy. The clamp may be drawn together like a screw clamp or forced together in a tong like device. An automatic downsizing to a desired degree of downsizing may be achieved by providing a suitable end position or stop of the clamp(s).

Cuff-Collar

A clamping collar may be positioned around the external features of the heart, probably around the AV groove or on the left ventricular free wall to push in the valve annulus anatomy and bring the annulus into the desired downsized shape for placement of a prosthetic device. The collar may be in the form of at least one, such as two opposed, encircling band elements. The collar may be of a shape to match the desired heart anatomy. The collar may be drawn together like a lasso, or be forced together in a tong like device or screw clamp device.

The cuff may be similar cuffs developed by Acorn Cardiovascular and Paracor to restrain the heart from further dilation, namely the HeartNet™ Device. The cuff device may be used to form the heart into the desired shape to shape the valve annulus appropriately for prosthetic device placement or another form of repair. An automatic downsizing to a desired degree of downsizing may be achieved by providing a suitable end position or stop of the cuff or collar.

D) Sinus Coronaries (Short Term Downsizing)

From the surface of the heart muscle force may be applied, reshaping the anatomic configuration of the myocardium. For the mitral valve it is possible to use the adjacent sinus coronaries as an access path, which is reachable via a minimal invasive method.

Long-term therapeutic devices using this access path for treating mitral insufficiency are e.g. disclosed in WO02/062270 of Solem and Kimblad. A device is disclosed in WO02/062270 for treatment of mitral annulus dilatation that comprises an elongate body having two states. In a first of these states the elongate body is insertable into the coronary sinus and has a shape adapting to the shape of coronary sinus. When permanently positioned in the coronary sinus, the elongate body is transferred to the second state assuming a reduced radius of curvature, whereby the radius of curvature of the coronary sinus and the radius of curvature as well as the circumference of the mitral annulus is reduced. The elongate body comprises a distal stent section, a proximal stent section and control wires between the two stent sections for reducing the distance between the distal and proximal stent sections for achieving the change of curvature.

Various shape effecting devices may be placed temporary in the sinus coronaries for a temporary downsizing effect facilitating an annuloplasty procedure. After terminating the procedure, the devices are then removed from the coronary sinus.

Figure 10:
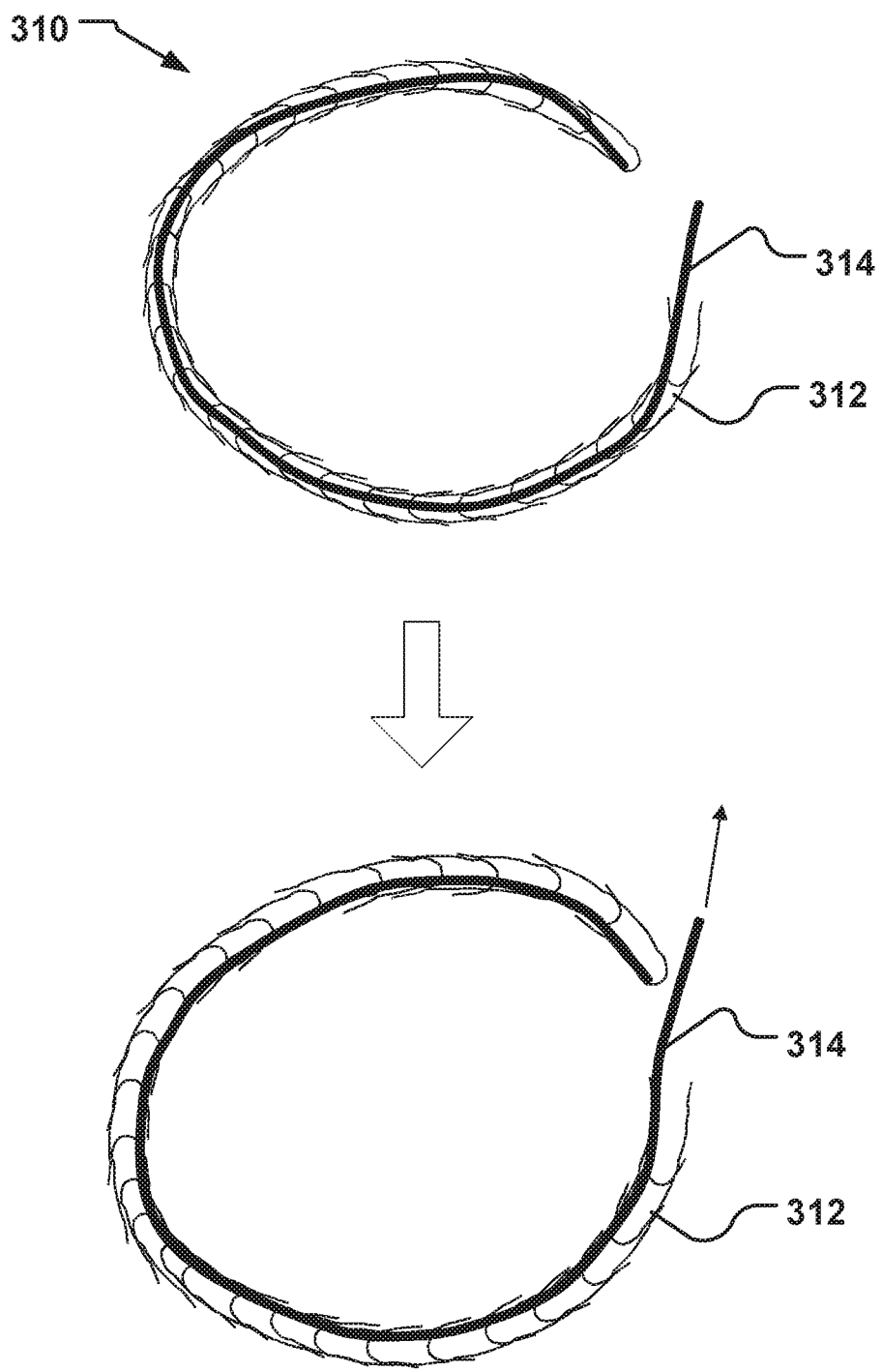
FIG. 10 is a schematic illustration of at least a part of another embodiment of the medical device providing a change of shape during use.

Tendons may be used for changing the shape of a medical device, such as shown in FIG. 10. In some embodiments of this type, the downsizing element comprises a plurality of segments 312 moveable in relation to each other, and a tendon 314 inserted along the plurality of segments 312, wherein the tendon is distally attached to a distal end portion of the downsizing element, such that the downsizing element decreases radially at least along a portion thereof upon pulling at a proximal portion of the tendon 314.

Electro Active Elements E.g. Micro Muscle

Electro active elements, e.g. polymeric elements as described above may be provided in elongate elements insertable into the sinus coronaries.

Rotating elements may be used for changing the curvature of downsizing elements insertable into the coronary sinus.

The above embodiments for insertion into the coronary sinus may make use of a temporary fixation element for facilitating the desired change of shape of the downsizing elements. For instance an inflatable balloon may be provided at a distal end of the device. Upon inflating the balloon, a fixation point is provided and the flexion of the temporary downsizing element is facilitated. When the annuloplasty procedure is finalized, the balloon is deflated again and the downsizing element is removed from the coronary sinus.

E) Circumflex Artery

Like the sinus coronaries, the circumflex artery may be used as an access path for temporary downsizing elements, devices or assemblies adapted for downsizing of an adjacent heart valve.

F) Myocardium Contraction

The myocardium (heart muscle) may be exposed to a stimulating element or agent resulting in a local contraction thereof providing a temporary downsizing. This may be provided both minimally invasive or during open chest cardiac surgery.

Electro Stimulation of Myocardium Causing Contraction of Annulus

The stimulation may be provided by electrical charges delivered locally to the myocardium, e.g. by means of an electrode. The electrode may be positioned in a catheter based minimally invasive manner.

Temperature Regulated

It is well known in the art that low temperature lowers the metabolic rate, in case of the heart the activity will slow down and time is gained whereby the surgery can be extended without damaging the heart. Cooling down the myocardium to approximately 22-24 degree Centigrade is used commonly during open heart surgery to cool down the entire heart.

Locally cooling down the cardiac tissue may be used to provide downsizing a valve annulus temporarily.

Chemical/Pharmacological

Various chemical substances or pharmacological agents may affect the contraction of the myocardium and provide downsizing of a valve annulus. The substances or agents may be delivered to the desired cardiac target site by a syringe needle or a hollow catheter e.g. having a hollow steerable needle tip, e.g. a smart needle.

Radiation

A further stimulus providing a temporary downsizing is radiation, e.g. from a radio frequency source.

Chordae tendinae are approximately 80% collagen, while the remaining 20% is made up of elastin and endothelial cells. By means of the above stimulations (temperature, chemical, RF), a part of the collagen may be temporary removed from the chordae for the downsizing. Collagen is rebuild after a certain time and restores function of the chordae.

G) Ventricular Free Wall Compression—Cuff

It may be suitable to temporary compress a free wall of the ventricle to reshape the dimension of the heart. The compression delivers a force uniformly over the area whereon the cuff is placed. With correct placement the shape of the annulus is affected, and downsizing of the same may be achieved.

H) Apical Elongation

The myocardium may be elongated, with the use of an external force, whereby the circumference of the myocardium at a cross-sectional plane close to the mitral valve and tricuspidal valve is reduced. Hence, these valves will be reshaped, and a downsizing may be achieved.

Mechanical

The force may be of a mechanical origin, as applying a pulling force at the apex cordis while fixating the superior part of the myocardium. The fixation of the pulling device at the apical area of the heart must be firm as well as gently in order not to harm the tissue.

Suction

In a similar setup, the force for fixation of the apical area may be provided utilizing a suction cup. By providing a vacuum, a secure fixation may be reached. Still a fixation of the superior part of the myocardium must be firm. While applying a pulling force at the apex cordis the rim of the suction cup together with the smoothness of the heart surface set boundaries to the amount of force the transition zone can bridge.

I) Pins or Theaters Across Left Ventricle

The heart muscle may be mechanically fixated by one or several pins though the whole extension of the heart, as well as the chordae. As the heart is fixated it may be compressed by applying force at each pin end, in a direction towards the centre of the heart. With suitable position of these pins a valve and corresponding annulus may be affected by the applied force, whereupon the valve is reshaped, and a downsizing may be achieved.

J) Atrial Compression

It may be suitable to temporary compress an atrium to reshape the superior dimensions of the heart. The compression may provide a force uniformly over the area whereon e.g. a cuff is placed. With correct placement the shape of the annulus is affected, and downsizing of the latter is achieved. Externally to the heart, ribbons or flexible bands may be positioned near or on top of the sinus coronaries to restrain the mitral valve. As the ribbon is tightened a compression force is applied to the mitral valve which may reduce its size. The method is however more rough than corresponding compression utilizing a cuff arrangement mainly because of two reasons: ribbons are most often small in width which may damage the tissue as the ribbons get tightened and the heart tissue may be callipered at the junction as well.

K) Balloon Under the Aortic Wall to Displace Annulus

With use of the aortic wall as a backbone, support, for a balloon, displacement of the aorta septal wall may be possible. The balloon will upon inflation, either by fluid as saline or other non-harming fluid or gas, induce a force towards the heart thereby causing a displacement of the heart structure. Although, the amount of displacement is dependent on the overall rigidity of both the heart muscle and the aortic wall. However rupture or weakening the aorta must be avoided.

Pulling Papillary Muscles

In a similar manner as the chordae tendinae may be circumflexed by devices and methods described herein, one or more papillary muscles may be circumflexed. For instance a lasso may be positioned around a single papillary muscle, or several papillary muscles, or all papillary muscles. Pulling the ends of the lasso arrangement and drawing towards the cardiac apex, i.e. away from the heart valve, may provide downsizing thereof. Helical devices may be provided and used for this purpose. An access way for such a device and method is via the apex through the myocardium. Transapical access is described below in more detail.

Parachute

The parachute technique may be simplified by embodiments of the present invention. The downsizing of an annulus may be provided prior to placing the sutures carrying an annuloplasty prosthesis. In this manner, the surgeon does not need to take into consideration a further change of shape of the annulus imposed by the position of the sutures. The alignment of the annuloplasty prosthesis is thus facilitated and the parachute procedure substantially simplified. For instance, the helical device is provided and used for this purpose.

For the parachute procedure, both ends of a single suture are sutured through the natural annulus, taking a relatively large gap between the needle penetration points. The two ends of this same suture are then passed through the prosthesis. The prosthesis is held away from the natural valve annulus during this procedure to allow easy access to the downsized annulus and the prosthesis. The prosthesis is easily aligned to the downsized annulus during this procedure, as the downsized annulus has a shape or contour adapted to that of the annuloplasty prosthesis. The suturing pattern is repeated using additional sutures, resulting in several suture "pairs" spaced around the downsized annulus. The prosthesis is then lowered or parachuted down against the downsized annulus. After all the suture pairs are secured, the result is a reduced annular circumference with an attached prosthesis. The downsizing medical device providing the downsizing may then be removed as the prosthesis now fixates the downsized shape permanently.

Access Routes For Downsizing

Percutaneous methods and techniques that may be applicable in downsizing a heart valve may be used. Even at open surgery it may be feasible to address the heart by some catheter based therapy. Access routes for the downsizing devices comprise the following routes, including catheter based therapy:

Trans Aortic (For Mitral)

A path to reach the mitral valve is by applying a transaortic approach entering the myocardium on the arterial side, reaching the mitral valve from beneath, the valve is upstream. The specific method is chosen to downsize the valve may be some of the above mentioned.

Trans Septal (For Mitral)

Another path to reach the mitral valve is by a trans septal approach, entering the myocardium on the venous side at the vena cava. The mitral valve is reached from beneath. The specific method chosen to downsize the valve may be some of the above mentioned.

Via Vena Cava, Trough Leaflets (For Tricuspid)

From the venous side the heart is reached via vena cava and entering the left atrium. The tricuspid valve is reached from above, trough the leaflets. The specific method chosen to downsize the valve may be some of the above mentioned.

Trans Apical (Both Mitral and Tricuspid)

In WO2005/104957, which is hereby incorporated by reference in its entirety for all purposes, it is disclosed how the mitral valve and the tricuspid valve can be reached from beneath by entering at the apical area of the myocardium, hence the valves are reached from below. It is suggested to enter percutaneously at the thorax at the fifth intercostal space, at the left side of the chest, other suitable entrance position are suggested as well. The suggested approach to reach the heart valves give possibilities to use larger surgical equipment than usually at percutaneous procedures. The lumen of the vessels normally sets an upper boundary on the equipment size. As the suggested approach of entrance is directly through the apical area of the heart, restrains are set by this anatomical structure. The specific method chosen to downsize the valve may be some of ones mentioned herein. A further detailed example of this access path is given below.

Figure 5A:
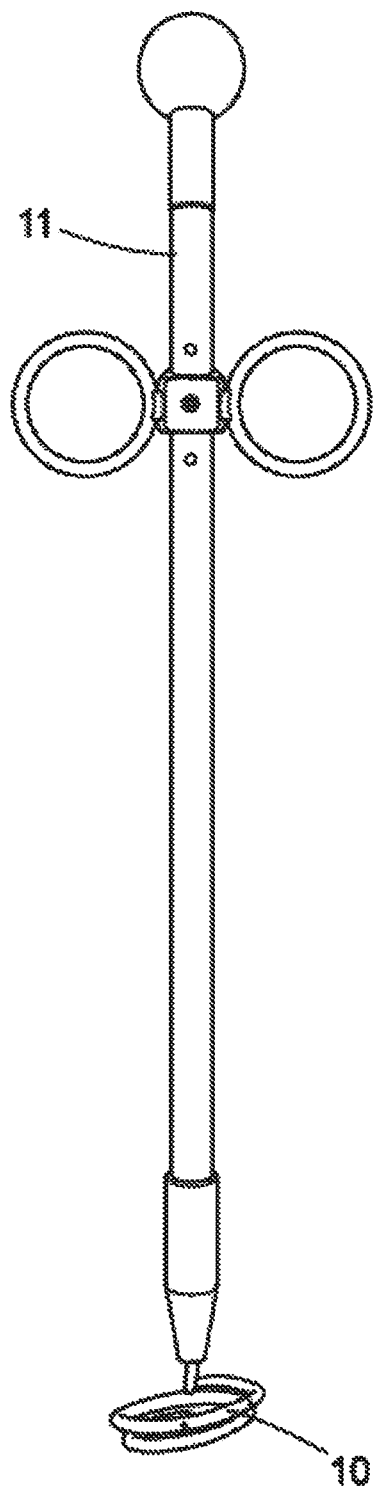
FIG. 5a is a lateral view of a medical device according to an embodiment of the invention, attached to a delivery device, here a delivery handle.
Figure 5B:
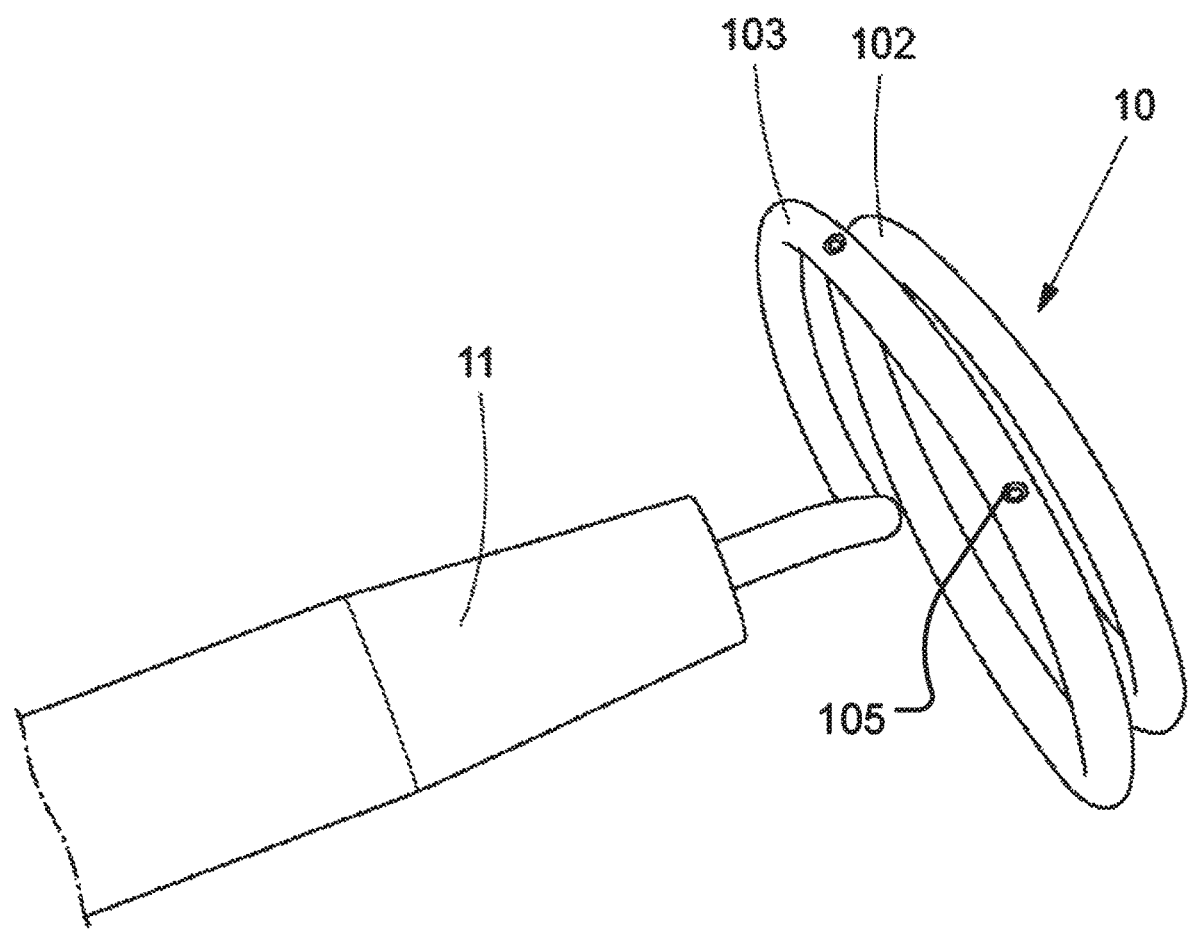
FIG. 5b is a perspective view of the medical device of FIG. 5a in an enlarged view.
Figure 6A:
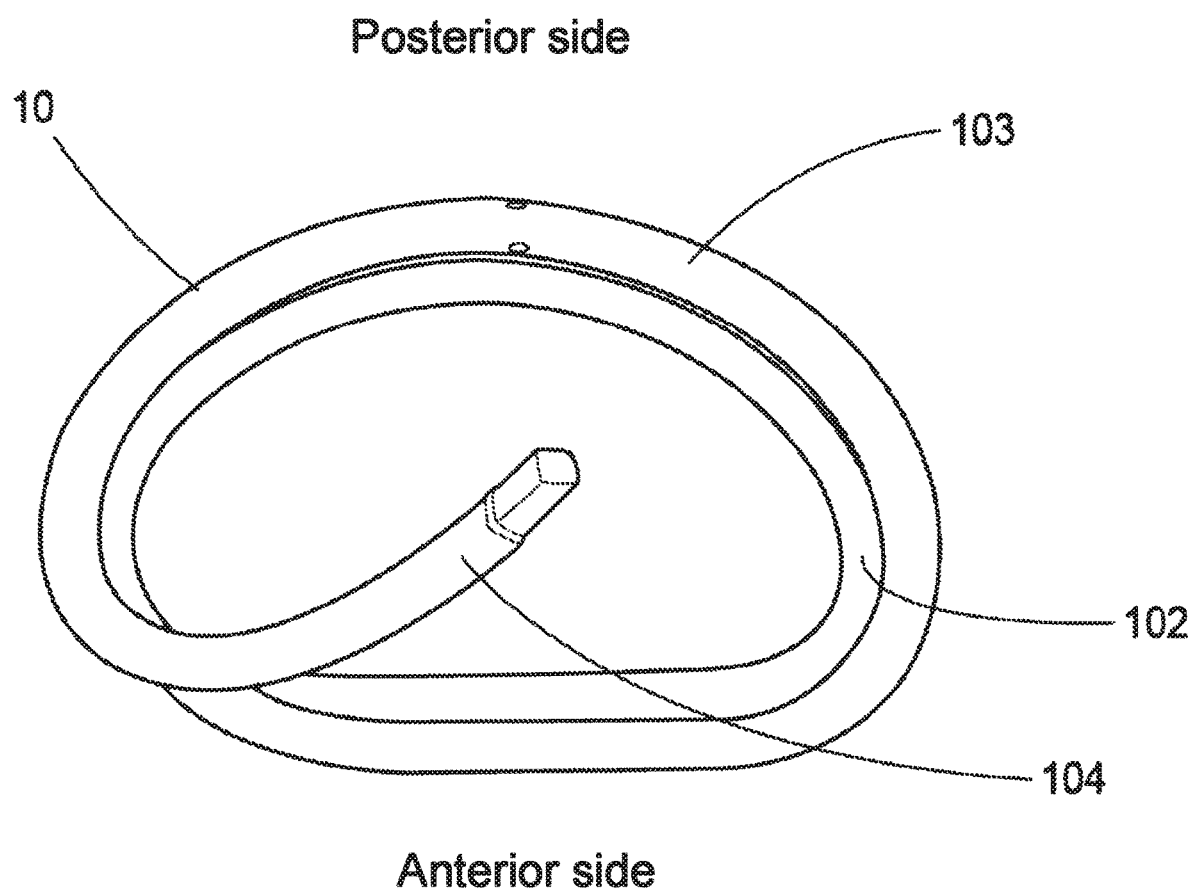
FIGS. 6a, 6b and 6c are detailed illustrations of the medical device according to FIG. 5b with the delivery device detached.
Figure 6B:
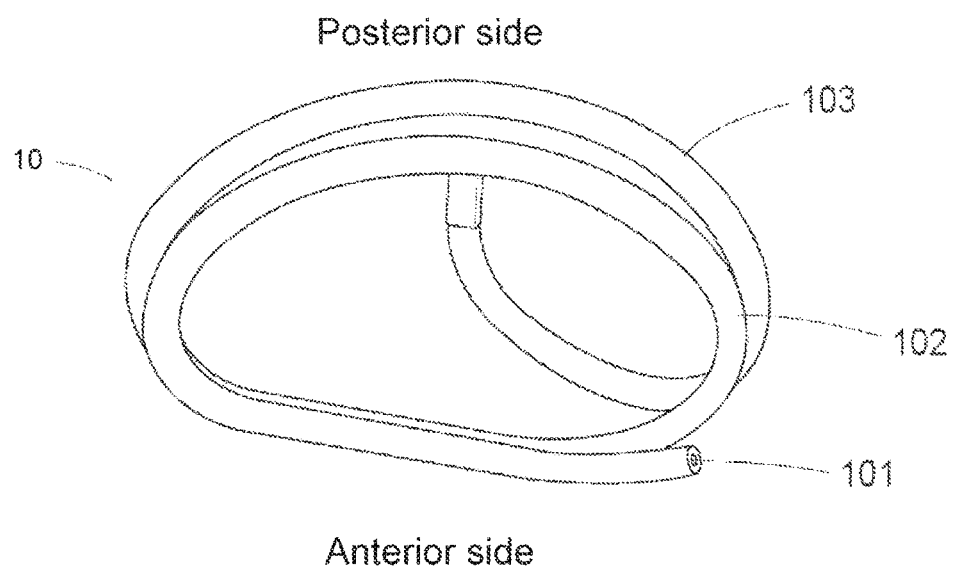
Figure 6C:
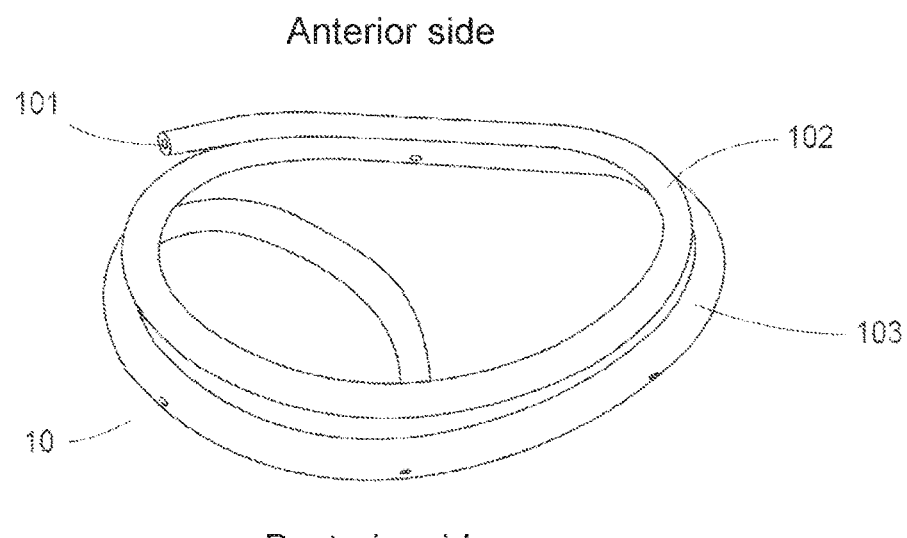

Now turning to FIGS. 5a to 6c, an embodiment of a medical downsizing device is described in more detail. FIG. 5a is a lateral view of a medical device 10 according to an embodiment of the invention, attached to a delivery handle 11. FIG. 5b is a perspective view of the medical device 10 of FIG. 5a in an enlarged view. FIGS. 6a, 6b and 6c are detailed illustrations of the medical device according to FIG. 5b without the delivery handle.

The medical device 10 is a pre annuloplasty downsizing device of the kind that is above referred to as helical or loop shaped device.

In more detail, the medical device 10 is a tool adapted to downsize a heart valve annulus for facilitating an annuloplasty procedure. The medical device 10 comprises a first and a second loop shaped, helical element 102, 103 assuming a helical structure on an imaginary cone and where a defined distance is kept between subsequent turns of the helix, i.e. a hollow centre and a free space between each turn. The medical device comprises further a proximal end 104 for releasably attaching a handle 20, and a distal end 101 in insertion direction of the medical device 10. Thus, the handle may be disengaged from the medical device 10. The cone shaped coil may resemble a spiral, helix like or keyring-type configuration. The second loop shaped element is connected to the first loop shaped element to form a coiled configuration, wherein the second loop shaped element is configured to be positioned on a second, opposite side oriented towards an atrium of the area of the valve tissue to thereby arrange the valve tissue between the first loop shaped element and the second loop shaped element, and wherein the second loop shaped element comprises at least one fixation element for releasable attachment of an annuloplasty implant or a heart valve prosthesis.

The first and a second loop shaped, helical elements 102, 103 may also be referred to as rings, laps or turns. The first ring is to be positioned within a cardiac chamber adjacent to, or in the vicinity of the valve tissue. The second ring, which at least partly may have a slightly larger circumference than the first ring, is to be positioned in the atrial side of the valve, i.e. adjacent to, or in the vicinity of the annulus of the valve. The distal end 101 of the helical medical device 10 is introduced at a commissure of the valve and rotated further for reaching its final position of use with the two helical elements 102, 103 on either side of the heart valve. Alternatively, the medical device may also penetrate the annulus of the heart valve instead of passing through the commissure. The positioning and downsizing procedure making use of the medical device 10 is explained in more detail below with reference to FIGS. 12 and 13.

The medical device 10 may comprise elements facilitating temporary fixation of other devices to the medical device 10. For instance through-holes 105 in the loop shaped elements, or selected portions thereof, may provide temporary fixation of other elements, such as an annuloplasty implant, and/or a heart valve prosthesis to the medical device 10, e.g. by means of sutures. In addition or alternatively other fixation means may be used for this purpose, such as clips, releasable staples, bands, etc. Also, the other element itself may be devised for the temporary fixation, e.g. by having a spring function temporary grabbing around one of the loop shaped elements. Upon delivery the other element may thus be removed from the medical device 10 to the site of implantation, e.g. by removing the fixation means, such as sutures, clips, etc. or by turning over, stretching, expanding, etc. the other element from the medical device 10 for fixation to the anatomical structure at the implantation site.

In some embodiments of the medical device, the distal end 101 is shaped in such a manner, that it catches the chordae (26, 28 for the mitral valve) by advancing between the chordae and the opposite cardiac muscle tissue 12. Thus the distal end 101 is arranged for catching the chordae inside the first helical element 102. The distal end 101 may for this catching purpose be directed radially outwards or axially downwards from a diametric plane of the second helical element 103.

The tip of the distal end 101 may be blunt, e.g. rounded, or provided with a spherical element. This provides for advantageous catching the chordae without risking injury or damaging the chordae or ventricular tissue.

At the proximal end 104, the device is provided with a connection interface for releasably attaching a delivery device, such as handle 11, such that a handling, direction and rotation is provideable to the medical device 10 in use thereof. In some embodiments, the delivery handle may be integral with the medical device 10. The proximal end 104 is arranged substantially perpendicular to a plane diametric to the loops of the medical device 10. The proximal end 104 may be arranged along a longitudinal axis imaginary arranged perpendicular to the plane diametric to the loops and in a center of the loops. Alternatively, the proximal end may also be arranged off-center, depending on the patient specific anatomical situation.

From the distal end 101 towards the connected second helical element 103, the body of the present embodiment of the medical device 10 extends along the first helical element 102 with a reduced radial extension. In this manner, upon further introducing the medical device 10, by rotating the latter, e.g. using the handle 11, in the rotational direction of the distal tip 101, the entire chordae of a heart valve are circumferentially gripped and upon rotation gradually moved towards the center of the medical device 10, defined by a longitudinal axis thereof. When one or more of the helical elements of the medical device has a non circular form, such as shown in FIGS. 6a to 6c, the movement of the chordae for the downsizing is dependent on the rotational direction of the medical device 10 in relation to the longitudinal axis of the medical device 10.

The effective turns (as e.g. shown in FIGS. 12 and 13) needed for providing a desired downsizing may be variable, including parts of turns, depending on the shape characteristics of the helical elements, e.g. their pitch, amount of taper of the helical windings, etc. For instance, the embodiments of the medical device may be rotated in full turns, quarter turns, half turns, multiple turns etc. In addition, or alternatively, a non-circular shape of at least a part of the helical windings may be used for providing a desired variable downsizing effect, depending on the degree of rotation when introducing the medical device 10. For instance, a D-shaped medical device 10, as illustrated in FIGS. 6a to 6c, may advantageously provide downsizing in a preferred direction, e.g. between the anterior side and the posterior side of the heart valve, e.g. for changing the shape of the mitral valve annulus in such a manner that two valve leaflets of the mitral valve are pushed towards each other without compressing the valve leaflets in the longitudinal direction thereof.

Figure 11:
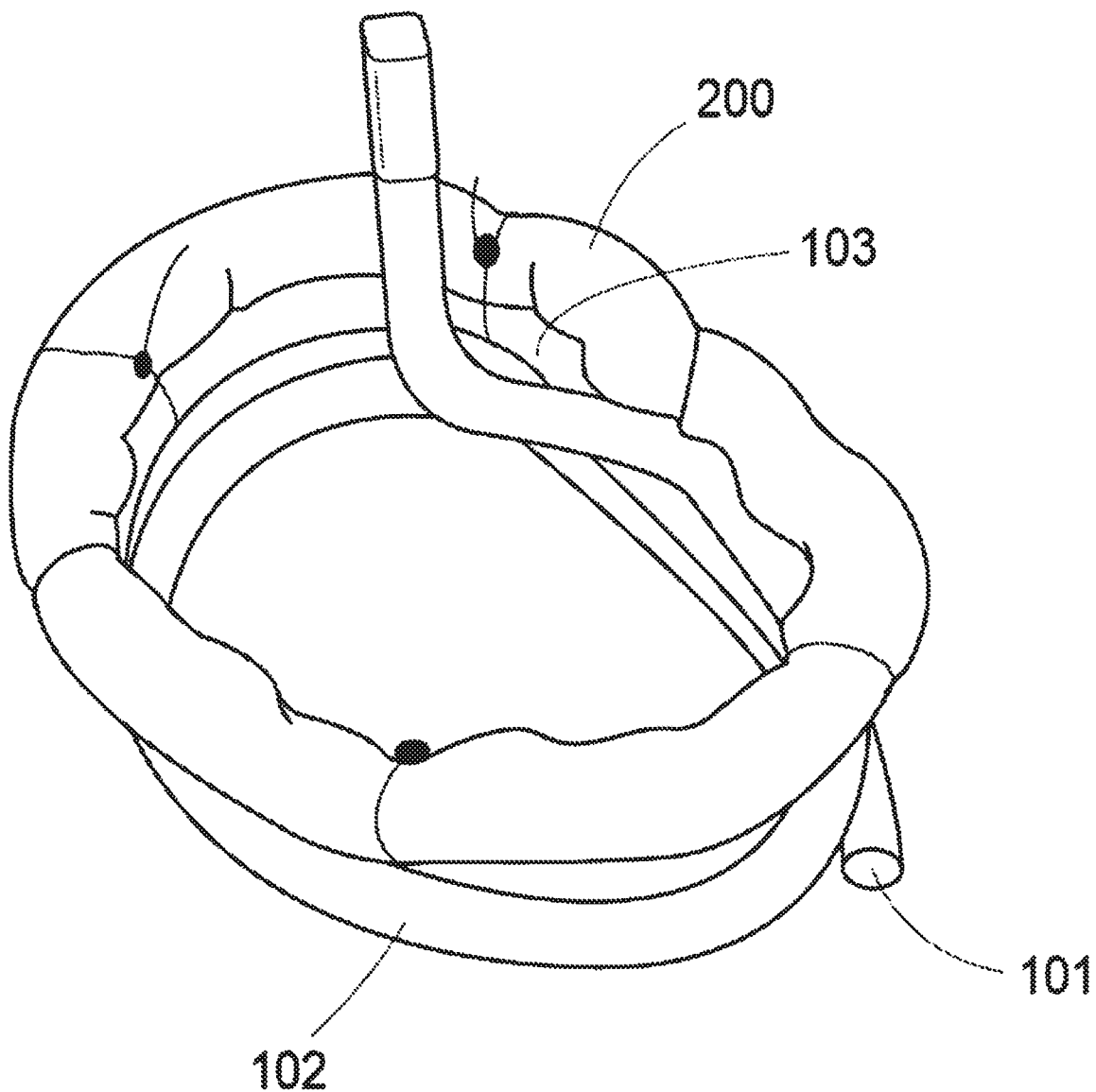
FIG. 11 is a perspective view of an embodiment of a medical device having an annuloplasty ring attached thereto.
Figure 12:
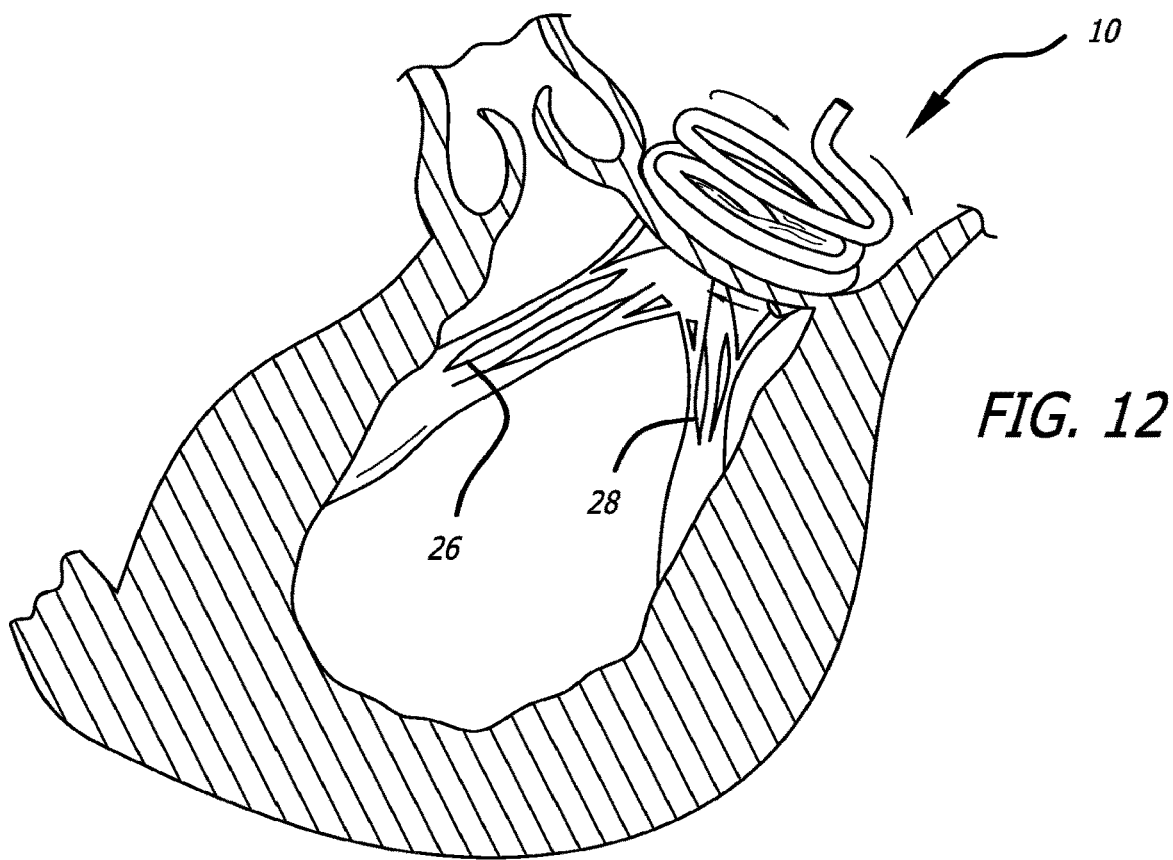
FIG. 12 is a schematic illustration showing the insertion of the medical device of FIGS. 6a-c for downsizing a mitral valve.
Figure 13:
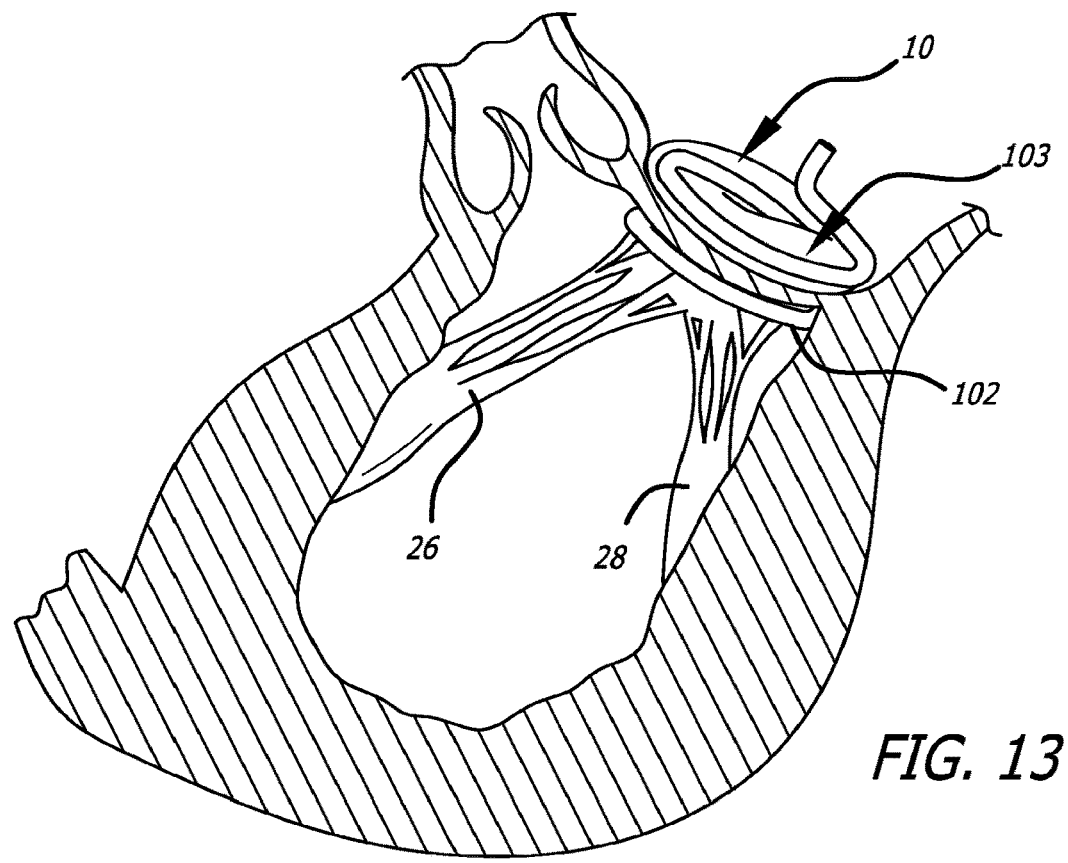
FIG. 13 is a schematic illustration showing the medical device of FIG. 12 inserted, circumflexing the chordae and providing the pre-annuloplasty downsizing of the mitral valve.

In some embodiments, an annuloplasty ring 200, see FIG. 7 or 11, may be temporary attached to the second helical element 103 and thus conveniently arranged for fixation to the valve annulus. Fixation of an annuloplasty ring to a valve annulus is e.g. described in WO2006/054930, which hereby is incorporated by reference in its entirety for all purposes. Holes may be provided in the second helical element 103 for providing temporary fixation points for the annuloplasty ring 200 to the medical device 10. For instance in FIG. 11, the fixation is illustrated with sutures that are removed upon downsizing of the valve annulus by means of the first helical element 102 and positioning of the annuloplasty prosthesis 200 at the annulus. FIG. 7 is a schematic view of the medical device of FIGS. 6a-6c with an annuloplasty prosthesis attached thereto, in use at a heart valve tissue.

The distal end 101 of the medical device is introduced through the commissure and is rotated to position, passing in between the heart muscle wall and the chordae. As the diameter is decreasing the chordae are pulled inward to the centre of the medical device and thus of the valve. Thus the valve annulus has been downsized to a desired degree allowing fixation of the shape and area thereof, e.g. by means of the annuloplasty prosthesis 200. When the annuloplasty prosthesis 200 is removed from the medical downsizing device 10 and fixated to the valve annulus, the medical device 10 is counter rotated and then withdrawn from the patient.

In this manner, a downsizing of the valve is automatically achieved in one step and the desired shape and area of the valve is provided for long-term fixation, e.g. by an annuloplasty ring.

In some embodiments, the downsizing may also be achieved in a long-term perspective for therapeutic purposes, thus further facilitating and simplifying the repair of regurgitation. In these embodiments, the medical downsizing devices are left in place at the termination of the medical valve repair procedure. This may be provided by disengaging a delivery unit, such as a handle or a catheter wire, from the downsizing element.

Any suitable medical grade material(s), such as medical grade metals or plastics, may be used to form the medical device 10. In some embodiments the medical device 10 may have a traditional cross sectional shape associated with a keyring. In this embodiment flat, opposed surfaces are arranged to be positioned on either side of a valve annulus tissue 20, the first ring in the cardiac chamber and the second ring in the atrium. The opposed surfaces 45 may also be roughened in order to improve engagement with the valve annulus 20. Viewed cross sectional, perpendicular to the longitudinal axis of the helical structure, the various embodiments of the invention may have a variety of geometric appearances e.g. circular, oval. Some embodiments may comprise changes of the cross sectional geometric form along the length of the medical device, e.g. the first and/or second ring may have different geometric shapes and varying cross sections, at least at portions thereof.

The annuloplasty implant 200 may be attached to the second helical element 103 of the medical device 10, by means of sutures or clips. The annuloplasty implant 200 may be any type of annuloplasty ring or band or C-formed band, such as the CG Future™ Annuloplasty System manufactured by Medtronic, Inc., the SJM Tailor® Annuloplasty Ring or the SJM Tailor® Flexible Annuloplasty Band manufactured by St. Jude Medical, Inc., the Sovering™ manufactured by Sorin Group, the Carpentier-McCarthy-Adams IMR ETlogix Annuloplasty Ring® or the Carpentier-Edwards Classic Annuloplasty Ring® manufactured by Edwards Lifesciences Corporation, which annuloplasty ring may form a complete ring-shape or an arcuate shape. The annuloplasty implant 200 is adapted to be attached to the valve annulus 20 by means of suture threads. The annuloplasty implant 200 has a shape conforming to a desired shape of the valve annulus 20. Thus, when attached to the valve annulus 20, the annuloplasty implant 200 will keep the, by downsizing reshaped, valve annulus 20 in the desired shape. The annuloplasty implant 200 is non-stretchable lengthwise, which implies that when attached to the valve annulus it will not allow dilatation of the annulus. However, the annuloplasty implant may be flexible to change its shape while maintaining its length to allow the normal movements of the valve annulus 20 during a heart cycle. The annuloplasty implant 200 may have sections of differing rigidity and flexibility to comply with the normal movements of the valve annulus 20 during the heart cycle.

Referring now to FIGS. 7-8a and 8b, a method for repairing a heart valve by means of embodiments of the medical device will now be described. First, access to the heart valve is achieved by conventional techniques, including arresting the heart and opening the chest. In FIG. 7, the device is shown when being inserted to the mitral valve 18. The distal end 101 of the first helical element 102 is brought to a corner of the opening between the leaflets 22, 24 of the mitral valve 18. The end 101 is led through the opening and the coil-shaped medical device 10 is turned, e.g. 360 degrees. Thus, the first helical element 102 is rotated into place on one side of the valve 18, whereas the second helical element 103 is placed on the opposite side of the valve 18. In this way, the medical device 10 is arranged in engagement with the valve 18, as shown in FIG. 7.

As shown in FIG. 8a the medical device is rotated into position and. Thereafter, the first helical element may be drawn towards the center of the medical device, drawing together the chordae, as shown in FIG. 8b.

The movement of the first helical element 102 towards the center of the device 10 may be implemented in various ways. In some embodiments a shape memory effect may be taken advantage of. In some embodiments, a tether line 314 may be used for drawing together a flexible first helical element 102, as shown in FIG. 10. In addition, or alternatively, the first helical element 102 may comprise a plurality of interconnected segments 312 allowing a change of shape of the first helical element 102, as shown in FIG. 10. In the embodiment shown in FIG. 10 only a single partial loop shaped element 310 is provided. Other embodiments may comprise several such loop shaped elements or only a portion thereof.

In some embodiments the medical device comprises of three rigid supporting elements, i.e. one added supporting element. Based on the helical structure the entire lowest ring has a diameter suited to be introduced in between the heart muscle wall and the most inner chordae tendinae for a heart with a dilated valve. The next lap has a smaller diameter in order to reduce the valve diameter. As for the above described embodiment a conventional annuloplasty ring 200 may be connected at the topmost lap of the device for delivery to the annulus.

In some embodiments, the medical device 10 may comprise a third helical element for providing a function of support rings, as described in WO2006/054930 with reference to FIG. 8 thereof. However, the leaflets 22, 24 need in the present embodiments not be drawn towards each other through a pinch of the support rings by means of a forceps instrument. The leaflets are already brought in a desired shape by the downsizing procedure. However, further adjustments may be made manually in this embodiment, if so desired. The support rings may be arranged to flex away from each other to allow drawing the leaflets 22, 24 through the pinch and to flex towards each other for preventing the leaflets 22, 24 to slip back. The valve annulus 20 may in this way be temporarily held in the new shape by means of the medical device 10 comprising two support rings configured to be arranged on opposite sides of the valve annulus and arranged to provide a releasable pinch between each other.

Figure 14:
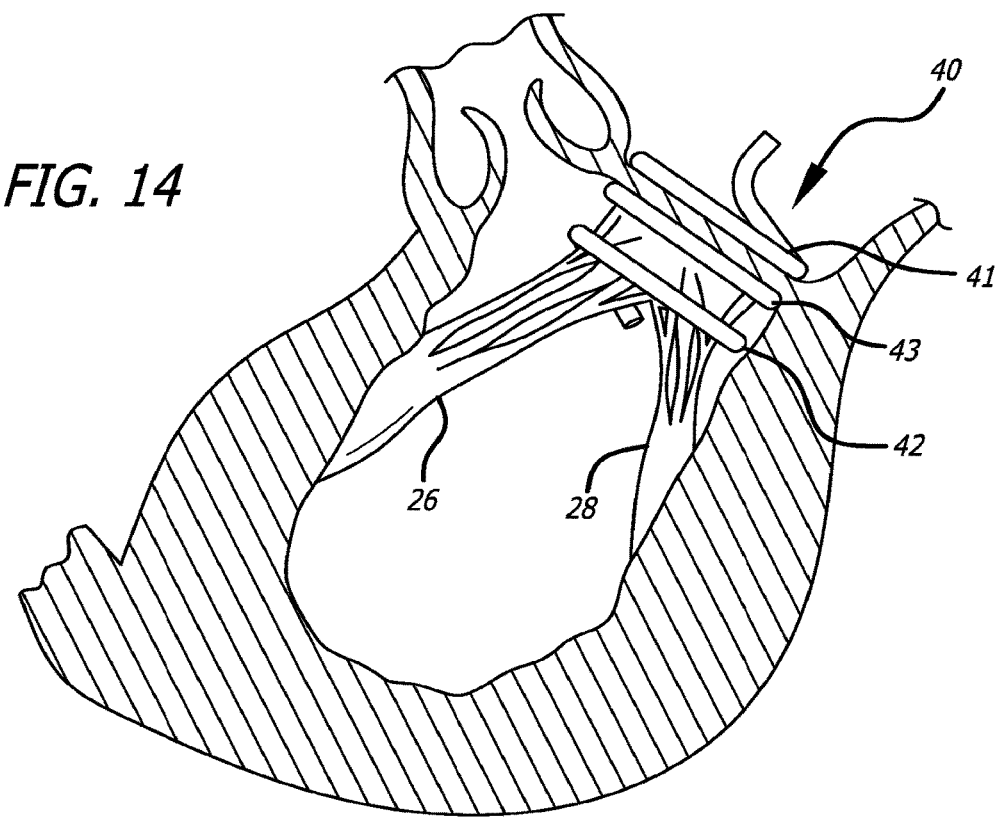
FIG. 14 is a schematic illustration similar to FIG. 13 showing another embodiment of a medical device inserted, circumflexing the chordae and providing a pre-annuloplasty downsizing of the mitral valve.

FIG. 14 is a schematic illustration showing an embodiment of a medical device of this type inserted, circumflexing the chordae and providing a pre-annuloplasty downsizing of the mitral valve. A first support ring 41 and a second support ring 43 are configured to be arranged on opposite sides of the valve annulus. The second support ring 43 provides the downsizing by circumflexing the chordae. A distal helical loop shaped element 42 provides for an advantageous insertion and circumflexing of the chordae, as well as variable downsizing, as explained above.

The support rings may have roughened, opposed surfaces to better keep the leaflets 22, 24 from slipping through the pinch and to hold the valve annulus 20 in its reshaped form. The annuloplasty implant 200, which has been carried into position by means of the second helical element, may now be attached to the valve annulus 20 for achieving a permanent reshaping of the annulus 20. Since a primary reshaping has already been made by the downsizing procedure, the positioning of the annuloplasty implant 200 is facilitated.

Figure 4:
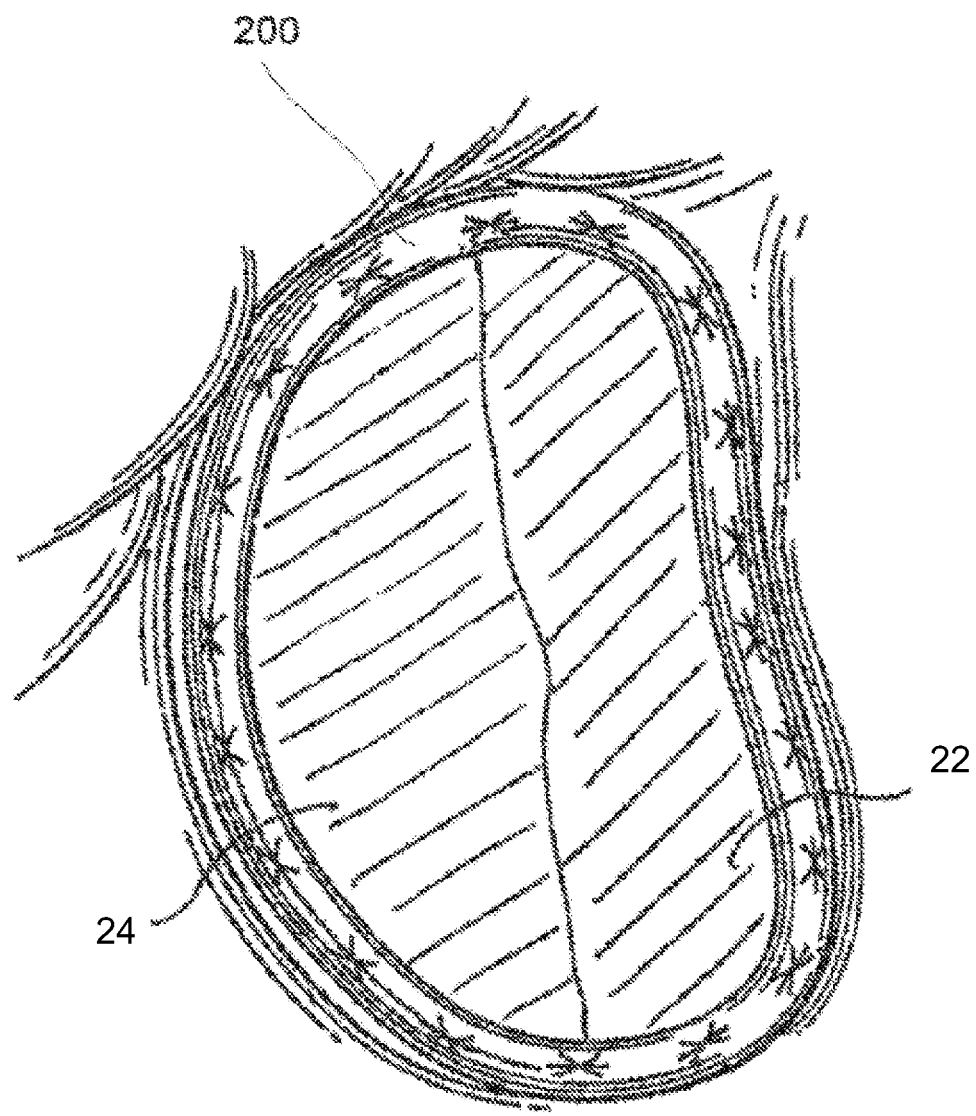
FIG. 4 is a planar schematic view of a mitral valve with an annuloplasty ring successfully arranged thereon, post downsizing and reshaping.

The annuloplasty implant 200 is then sutured to the valve annulus, as illustrated in FIG. 4, showing a completed suture 60 attaching the annuloplasty implant 200 to the valve annulus 20 and showing a suture being performed. In this way, the annuloplasty implant 200 is firmly attached to the valve annulus 20 for keeping the valve annulus 20 in its reshaped form.

When the annuloplasty implant 200 has been firmly attached to the valve annulus 20, the annuloplasty implant 200 is released from the medical device 10. The sutures holding the annuloplasty implant 200 attached to the second helical element 103 are cut in order to release the annuloplasty implant 200 from the medical device 10. Now, the medical device 10 may be withdrawn. The medical device 10 is turned 360 degrees in order to rotate the first helical element 102 to be retracted through the opening between the leaflets 22, 24. Thereafter, the medical device 10 may be retracted from the patient, e.g. by means of handle 20. As shown in FIG. 4, the annuloplasty implant 200 is now left in the patient holding the valve annulus 20 in a reshaped form such as to function normally.

In some embodiments, the first element of the medical device is at least partly made of a shape memory material, such as a shape memory alloy or a shape memory polymer (SMP) configuration, wherein the SMP in some embodiments may be radio-opaque. While insertion of the medical device though one of the valve's commissure into the interspace between chordae tendinae and the heart muscle wall, the first element is configured to have a larger curvature which may facilitate a more easily surgical procedure for the surgeon. After the medical device is correctly placed in the aforementioned anatomical void, the surrounding heat from the patient causes the device to assume a smaller diameter, corresponding to a memory shape previously set, and hence a downsizing of the valve is achieved in an advantageous manner. In more detail, some embodiments of the medical device comprise a downsizing element that comprises at least a portion of a shape memory material. In some embodiments, a first loop shaped element has a first shape configured to facilitate easy access of the chordae 26, 28 and a second shape, obtained by a change of shape of the portion of the shape memory material, configured to reposition the chordae 26, 28 towards a centre of the valve. In some embodiments the first loop shaped element is radially moveable with respect to the second loop shaped element. The downsizing element may be adjustable in a diameter thereof to provide adjustment of the annulus for the downsizing.

Figure 9:
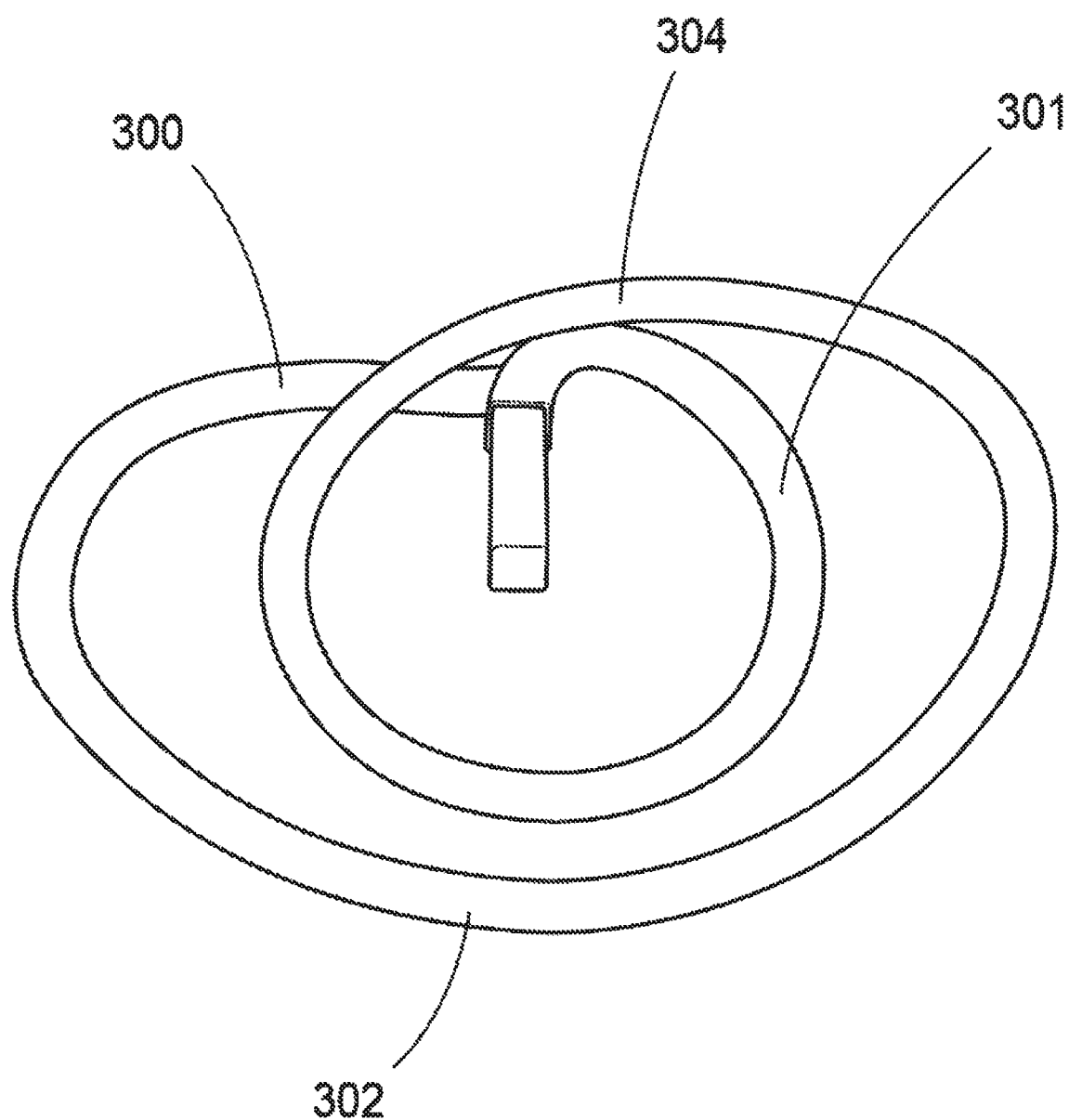
FIG. 9 is a schematic illustration of another embodiment of a medical device for insertion to the ventricular side of a heart valve.

FIG. 9 is a schematic illustration of another embodiment of the medical device for insertion to the ventricular side of a heart valve. The medical device 300 comprises a proximal end 301, and a helical loop 302, and a transition section 304 there between. As the diameter of the transition section gradually decreases, the downsizing achievable by the medical device 300 is depending on how far it is rotated, and thereby the rate of downsizing is controllable.

Controllability and repeatability of the downsizing may in embodiments be provided by a unit indicating the rate of downsizing, e.g. a scale indicating the position of the device relative anatomical structures, such as the chordae, annulus or valve leaflets; or a unit indicting the rotational angle of the medical device 300 upon insertion; a conically coiled downsizing element wherein a degree of the cone in relation to the valve corresponds to the degree of downsizing.

Figure 15:
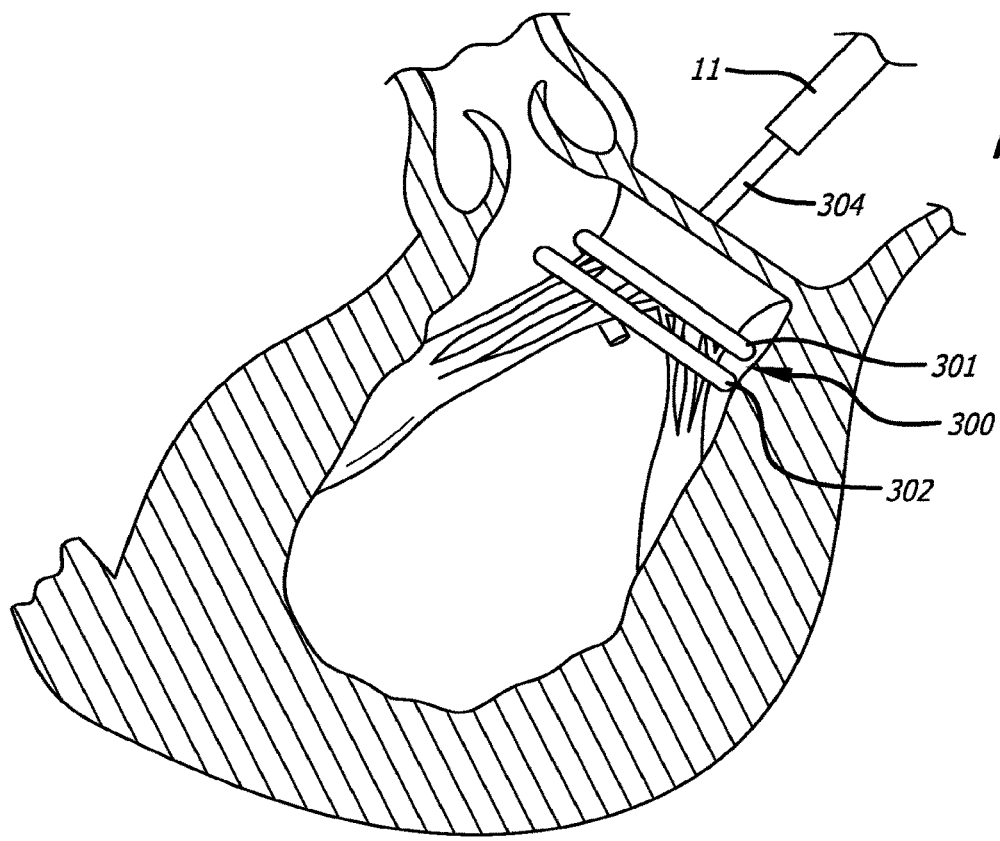
FIG. 15 is a schematic illustration similar to FIG. 13 showing another embodiment of a medical device inserted, circumflexing the chordae and providing a pre-annuloplasty downsizing of the mitral valve.
Figure 16:
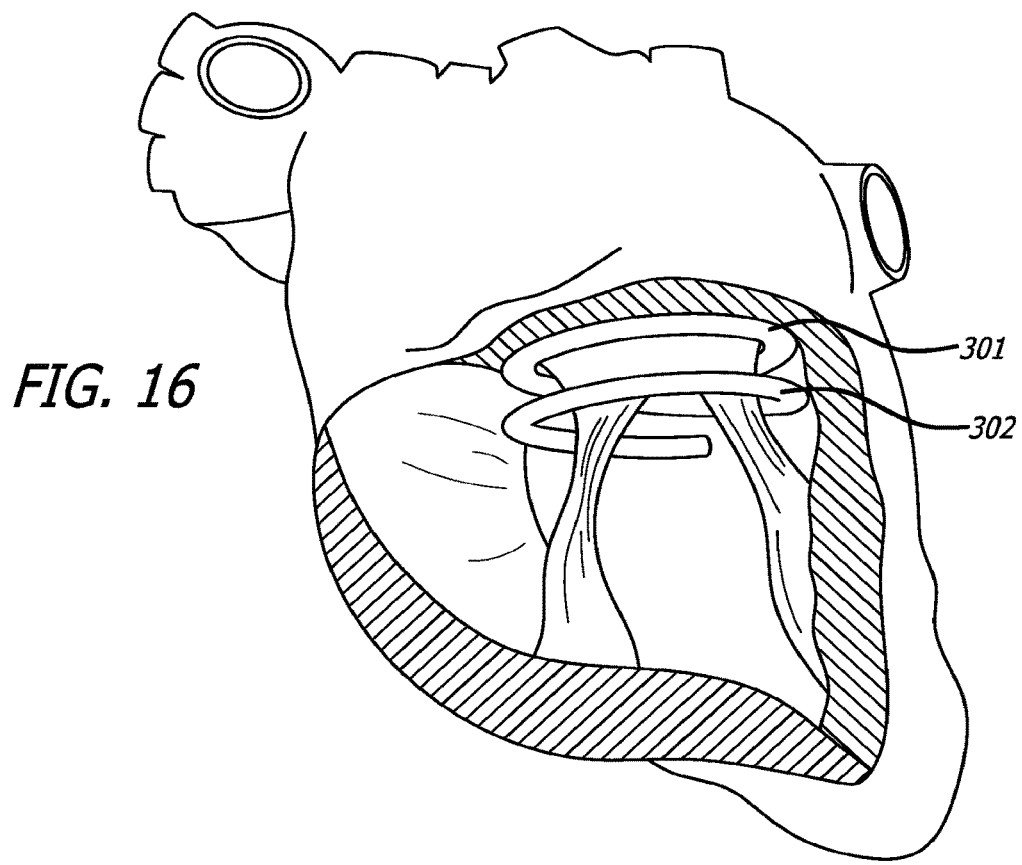
FIG. 16 is a perspective view of a heart showing the situation of FIG. 15 in perspective.

FIG. 15 is a schematic illustration showing the medical device 300 inserted, circumflexing the chordae and providing a pre-annuloplasty downsizing of the mitral valve. FIG. 16 is a perspective view of a heart showing the situation of FIG. 15 in perspective. It becomes evident that the distal end of the medical device 10 advantageously is insertable into the interspace between the chordae and the myocardium.

FIG. 17 is schematic illustration of another device providing pre-annuloplasty downsizing. The device 50 may for instance be a lasso, or similar, as described above.

Figure 18:
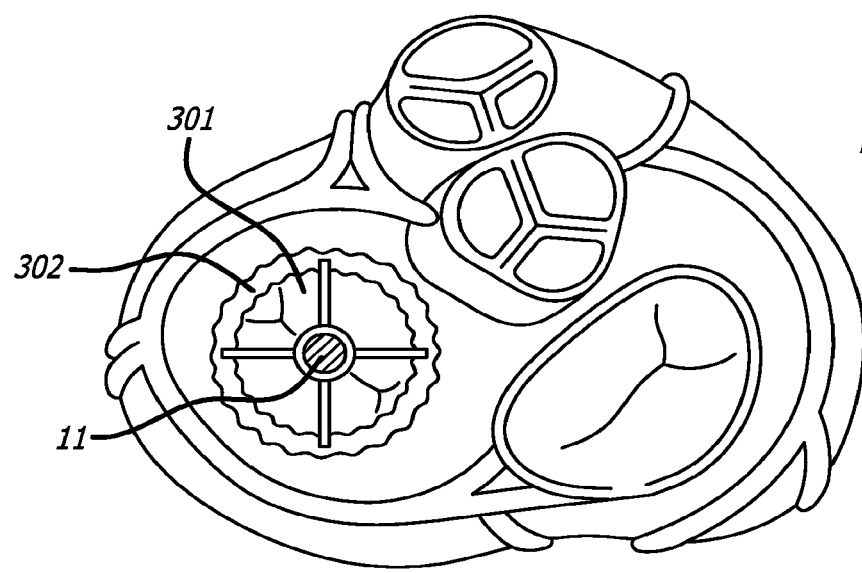
FIG. 18 is a view from above showing another medical device providing downsizing and positioning of an annuloplasty prosthesis with a single delivery device.
Figure 19:
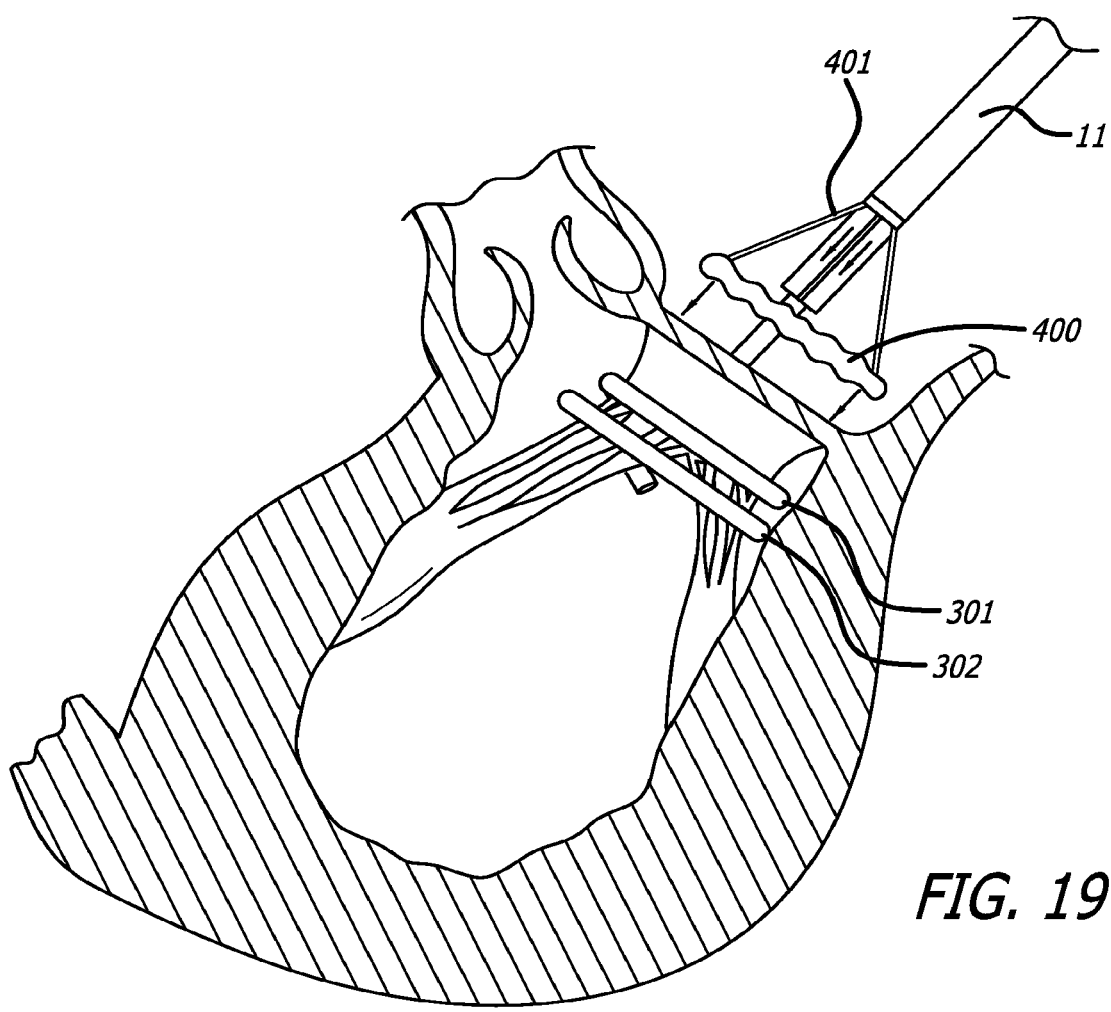
FIG. 19 is a schematic lateral view illustrating the annuloplasty prosthesis and the medical device of FIG. 18 in the pre-annuloplasty downsized configuration prior to positioning and fixating the annuloplasty prosthesis.

FIG. 18 is a view from above showing another medical device providing downsizing and positioning of an annuloplasty prosthesis with a single delivery device 11. An annuloplasty prosthesis 400 may be arranged longitudinally movable along an elongated section of the delivery device 11. In use, the downsizing is first achieved by the loops 301, 302 as described above. The annuloplasty prosthesis 400 is then lowered into position and fixates the valve annulus. Subsequently, the annuloplasty prosthesis 400 is released from the tool 11, e.g. by cutting connection elements 401, such as threads or wires. FIG. 19 is a schematic lateral view illustrating the annuloplasty prosthesis and the medical device of FIG. 18 in the pre-annuloplasty downsized configuration prior to positioning and fixating the annuloplasty prosthesis.

Alternatively, the medical device 10 does not carry the annuloplasty implant 200. In this case, the medical device 10 is inserted into position first. This positioning of the medical device 10 may be performed as described above with reference to FIG. 7. While the medical device 10 is held in place maintaining the temporary reshaping of the valve annulus 20, the annuloplasty implant 200 may be inserted to the valve to be treated by means of conventional techniques for inserting an annuloplasty ring. The annuloplasty implant 200 is then sutured to the valve annulus in order to permanently keep the valve annulus 20 in its reshaped form. Thereafter, the medical device 10 may be withdrawn leaving the annuloplasty implant 200 in the patient.

In some embodiments a kit for repairing a heart valve comprised of valve tissue including an annulus and a plurality of leaflets for allowing and preventing blood flow is provided. The kit may comprise a medical device for facilitating a repair and/or replacement of a defective heart valve of a heart of a patient, the device comprising a downsizing element devised to automatically provide downsizing of an annulus of the heart valve upon insertion of the downsizing element into the heart; and an annuloplasty implant adapted to be attached to the heart valve annulus in order to reshape the annulus and allow the leaflets to open and close properly, and/or a valve prosthesis adapted to be attached to the heart valve annulus or the annuloplasty implant in order to allow the heart valve to open and close properly.

The medical device may in specific embodiments be any of the above described medical devices comprising a downsizing element.

In the kit the annuloplasty implant and/or the valve prosthesis may be arranged movable along the medical device upon the downsizing and into position for fixation to the annulus, and arranged releasably to the medical device for the fixation, such as described with reference to FIGS. 18 and 19.

In the kit the annuloplasty implant and/or valve prosthesis may be releasably attached to the medical device by means of sutures, clips or staples.

In the kit the downsizing device, annuloplasty implant and/or valve prosthesis may be patient configured.

In the kit the device may be arranged to be withdrawn from the patient after the annuloplasty implant and/or valve prosthesis has been fixated to the valve tissue.

The medical devices of embodiments may be used in a method for repairing and/or replacing a heart valve comprised of valve tissue including an annulus and a plurality of leaflets for allowing and preventing blood flow, the method comprising: inserting a medical device for automatically downsizing the annulus of the heart valve upon insertion of the medical device and prior to fixating an annuloplasty implant and/or valve prosthesis to the heart valve.

The method may comprise accomplishing the automatically downsizing by means of a downsizing element of the medical device devised to provide the automatically downsizing of an annulus of the heart valve upon insertion of the downsizing element into the heart.

The method may comprise accessing and circumflexing all chordae 26, 28 of the heart valve by the downsizing element and temporary repositioning the chordae 26, 28 of the heart valve by the downsizing element upon insertion thereof.

In the method the reposition of the chordae 26, 28 may comprise repositioning the latter towards a centre of the valve upon the insertion of the medical device to provide the downsizing.

In the method the inserting may comprise inserting a distal end of the medical device through a portion of the valve tissue, rotating the medical device to position the distal end on a first side of the valve, and downsizing the annulus from the first side of the valve.

Figure 20:
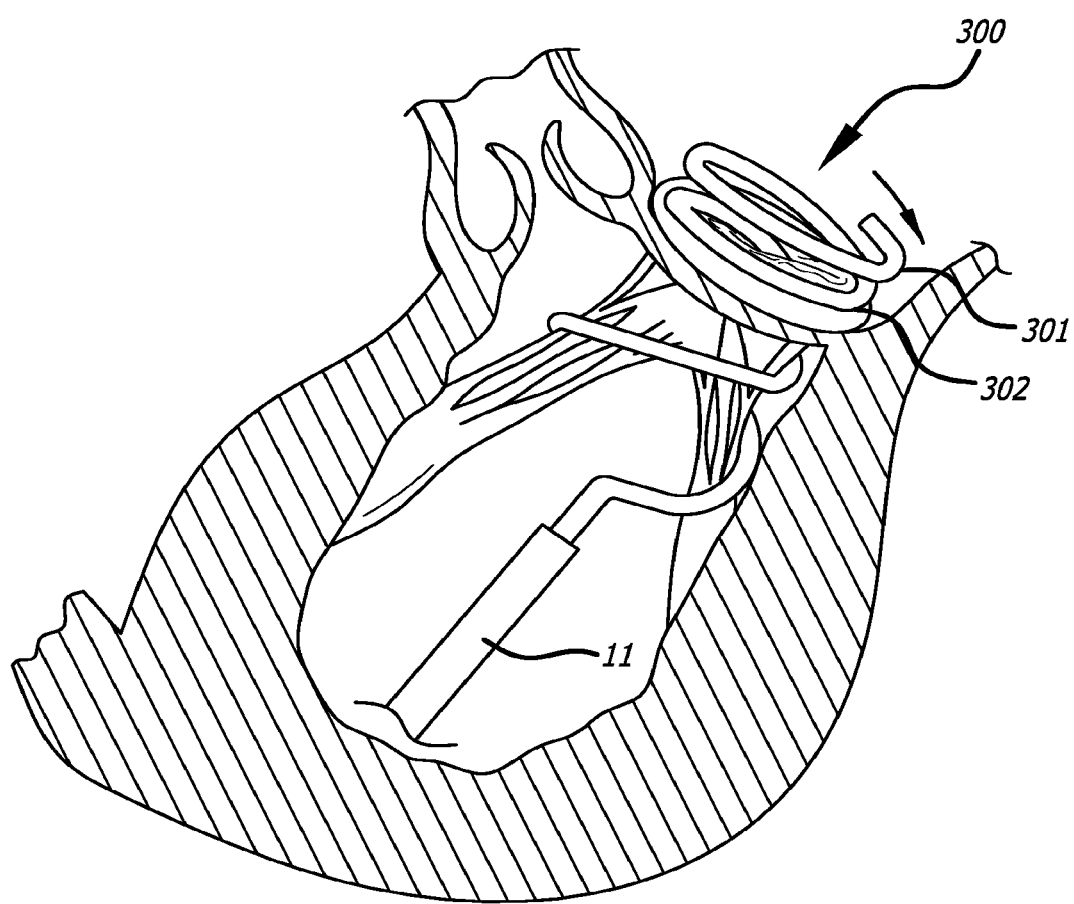
FIG. 20 is a schematic illustration of a medical device providing downsizing via a ventricular access to a cardiac valve.

FIG. 20 is a schematic illustration of a medical device 300 providing downsizing via a ventricular access to a cardiac valve.

Thus, in a method a downsizing element is provided via ventricular access.

The downsizing medical device 300 might be introduced transapically through a ventricle towards the valve. Here, a surgical cut is made in the apex of the ventricle, and widened by a dilator, for access of the tool. The tool may then conveniently be inserted through the transapical opening, e.g. intercostally or from a sub sternal incision via an opening in the epicardium. When the tool is retracted, or left in place, e.g. for annuloplasty and/or valve replacement, the delivery device, such as handle 11, is conveniently removed, and the incision is safely closed before finalizing the medical procedure.

The downsizing element may be introduced via a transmuscular access through the ventricle wall. For instance when having overdilated heart muscle tissue, an aneurysm may occur. Such diseased heart muscle tissue is often surgically removed. Before closing the opening in the heart muscle, access is provided to the interior of the ventricle and to the heart valves.

When the downsizing element is inserted into the ventricle, it may be rotated or change shape to circumflex the chordae 26, 45. Upon rotation towards the valve, downsizing is achieved. The medical device may then be further rotated, through a commissure of the valve, e.g. for delivery of an annuloplasty ring and/or artificial heart valve. Thanks to the anatomical arrangement of the chordae and commissures, the chordae automatically guide the distal end of the medical device 300 towards and into the commissure through the valve. This is in particular advantageous as performance of the procedure becomes very convenient.

Alternatively, when the downsizing element is inserted into the ventricle, it positioned distally through the valve. There it may change shape to the helical configuration. Upon rotation back towards and through the valve, downsizing is achieved.

Present methods and devices may eliminate a number of previous uncertainty factors or inconveniencies. A correct size of an annuloplasty device and/or heart valve is provided. Hitherto surgeons determined the correct size by a trial and error principle, testing different sizes of annuloplasty devices until a correct one was found for implantation. This is now avoided. The correct size may be provided by a unit indicating the rate of downsizing, and choosing a corresponding annuloplasty device and/or heart valve. Alternatively, an annuloplasty device and/or heart valve may be affixed to the medical device 300, as described above. In this case, the annuloplasty device and/or heart valve automatically have the correct size, as the size is determined by the downsizing element.

The downsizing element may be rotated into position. The correct downsizing is checked. If not satisfactory, a further up/down rotation is provided until an acceptable downsizing is provided by a correct coaptation. The downsizing element may then be removed, an annuloplasty device releasably fixed to it at a position for correct release at the downsized valve. Then the downsizing element is rotated back into the previously determined correct position, and the annuloplasty device is implanted or fixated to the annulus.

A successful procedure may be tested by supplying a liquid into the ventricle, and subsequently pressurizing the ventricle. In this manner, a leakage is detectable by liquid passing a valve area, e.g. via a paravalvular leakage. Detected leakages may then be attended to. Leakages may for instance be prevented by using specific flange units on annuloplasty devices, such as described in PCT/EP2007/062225, which hereby is incorporated by reference in its entirety for all purposes.

It should be emphasized that the embodiments described herein are in no way limiting and that many alternative embodiments are possible within the scope of protection defined by the appended claims.

For example, the access to the heart valve may be achieved endoscopically. In such case, the medical device 10 and/or the annuloplasty implant 200 need to be inserted through a narrow tube (catheter). This implies that the medical device 10 and perhaps the annuloplasty implant 200 will need to be compressed during insertion in order to pass through the catheter. The medical device 10 needs to assume its proper shape after having been passed through the endoscope. Therefore, using a catheter based approach, the medical device 10 should preferably be formed from a shape memory material. This allows the medical device 10 to be compressed and also to have a stable shape when being applied to the heart valve. Further, the annuloplasty implant 200 needs to be flexible in order to be compressed for the insertion through the endoscope.

The medical device 10 may also be produced as a patient configured device. Production of the medical device 10 may for instance be based on production data derived from virtual planning a heart valve repair and/or replacement based on 3D image data, such as patient image data acquired by an image modality, such as Magnetic Resonance (MR) Imaging, Computed tomography (CT), or Ultrasound. The medical device 10 may be produced at the patient examination site where the images are acquired, which save transport time. Alternatively, the production data may be generated or transmitted to a remote production site of the medical device 10. A patient configured device further minimizes the time needed for the medical procedure, providing all advantages related thereto.

The aforementioned downsizing devices and methods are applicable in a variety of clinical indications:

Mitral regurgitation (MR) is a valvular heart disease also known as mitral insufficiency, which is an abnormal leaking of blood through the mitral valve, namely from the left ventricle into the left atrium of the heart. For instance, a dysfunction of the valve leaflets, the mitral valve annulus, the papillary muscles, and the chordae tendinae can cause mitral regurgitation. The chordae tendinae, or heart strings, are cord-like tendons that connect the papillary muscles to the tricuspid valve and the mitral valve in the heart.

Many causes for mitral regurgitation exist, e.g. myxomatous degeneration of the valve, which is a genetic abnormality affecting the collagen that makes up the mitral valve. This causes a stretching out of the leaflets of the valve and the chordae tendinae. The elongation of the valve leaflets and the chordae tendinae prevent the valve leaflets from fully coapting when the valve is closed, causing the valve leaflets to prolapse into the left atrium, thereby causing mitral regurgitation.

Ischemic heart disease may cause mitral regurgitation by the combination of ischemic dysfunction of the papillary muscles, and the dilatation of the left ventricle that is present in ischemic heart disease, with the subsequent displacement of the papillary muscles and the dilatation of the mitral valve annulus.

Secondary mitral regurgitation may be present due to the dilatation of the left ventricle, causing stretching of the mitral valve annulus and displacement of the papillary muscles. This dilatation of the left ventricle can be due to any cause of dilated cardiomyopathy, including aortic insufficiency, nonischemic dilated cardiomyopathy and Noncompaction Cardiomyopathy. Dilated ventricles may be surgically treated by removing a portion of the ventricular muscle tissue.

When the right ventricle of the heart contracts, the blood pressure pushes the tricuspid valve which closes and prevents a backflow of blood into the right atrium. The chordae tendinae prevents the flaps from being everted into the right atrium. Similarly, these cord-like tendons hold in position other flaps like the bicuspid or mitral valve. Many causes also exist for tricuspid dysfunction, but will not be elucidated herein in more detail.

The present invention has been described above with reference to specific embodiments. However, other embodiments than the above described are equally possible within the scope of the invention. The different features and steps of the invention may be combined in other combinations than those described with reference to specific embodiments. Features of embodiments may advantageously be interchanged or combined. The scope of the invention is only limited by the appended patent claims.

The invention claimed is:

1. A kit for repair and/or replacement of a native mitral valve, the kit comprising:
   a loop-shaped element comprising:
   a proximal end;
   a distal end; and
   a curved body extending between the proximal and distal ends, the curved body comprising a proximal portion, a distal portion, and a middle portion extending between the proximal portion and the distal portion, wherein:
   the proximal portion extends from the proximal end and is sized for positioning on an atrial side of the native mitral valve;
   the distal portion extends from the distal end and is sized for positioning on a ventricular side of the native mitral valve;
   the proximal portion, the distal portion, and the middle portion are formed continuously to form the curved body;
   the middle portion is configured to extend through a natural opening in the native mitral valve;
   the distal portion comprising first and second curved regions, the first curved region extending between the distal end and the second curved region, the first curved region having a first radius of curvature that is larger than a second radius of curvature of the second curved region;
   the first radius of curvature is sized so that during delivery of the loop-shaped element to the native mitral valve, the distal portion passes between native heart muscle wall and chordae of the native mitral valve so as to circumflex the chordae of the native mitral valve when the distal portion rotates into place at a ventricular side of the native mitral valve;
   the curved body comprising a substantially helical shaped portion having at least two full turns around a center axis that is substantially perpendicular to a plane diametric to the at least two full turns of the curved body, and a portion extending in parallel to the center axis and off-center from a center of the at least two full turns of the curved body; and
   a mitral valve prosthesis configured for fixation at the native mitral valve,
   wherein the distal end is arranged radially outwards or axially downwards from a diametric plane of the distal portion of the loop-shaped element, so as to circumflex the chordae.

2. The kit according to claim 1, wherein the proximal end of the loop-shaped element comprises a connection interface configured to releasably attach to a delivery device.

3. The kit according to claim 1, wherein the distal portion of the loop-shaped element further includes a transition region arranged between the first curved region and the second curved region, wherein the transition region has a radius of curvature that gradually decreases from the first radius of curvature to the second radius of curvature.

4. The kit according to claim 1, wherein at least some of the distal portion has a non-circular shape.

5. The kit according to claim 1, wherein at least some of the proximal portion has a non-circular shape.

6. The kit according to claim 1, wherein the loop-shaped element is configured to be compressible for delivery in a catheter.

7. The kit according to claim 6, wherein the loop-shaped element is formed from a shape-memory material.

8. The kit according to claim 1, wherein the loop-shaped element includes sections of differing rigidity.

9. The kit according to claim 1, wherein the loop-shaped element includes sections of differing flexibility.

10. The kit according to claim 1, wherein the distal portion of the loop-shaped element is configured to reposition the chordae towards a center of the native mitral valve.

11. The kit according to claim 1, wherein the mitral valve prosthesis is configured to be attached to the loop-shaped element.

12. The kit according to claim 11, wherein the mitral valve prosthesis is configured to be inserted along the center axis of the loop-shaped element to place the mitral valve prosthesis into position at the native mitral valve.

13. The kit according to claim 1, wherein upon positioning the distal portion at the ventricular side of the native mitral valve and positioning the proximal portion at the atrial side of the native mitral valve, native valve tissue is arranged between the distal and proximal portions of the loop-shaped element.

14. The kit according to claim 13, wherein the distal portion and proximal portion are arranged to provide a releasable pinch.

15. The kit according to claim 1, wherein the substantially helical shaped portion has at least two and a half turns.

16. The kit according to claim 1, wherein the portion of the curved body extending in parallel to the center axis is arranged as part of the proximal portion of the loop-shaped element.

17. The kit according to claim 16, wherein the portion of the curved body extending in parallel to the center axis is arranged at the proximal end of the loop-shaped element.

18. The kit according to claim 1, wherein at least the middle portion of the curved body is included in the substantially helical shaped portion of the curved body.

19. The kit according to claim 18, wherein at least a part of the distal portion of the curved body is included in the substantially helical shaped portion of the curved body.

20. The kit according to claim 19, wherein at least a part of the proximal portion of the curved body is included in the substantially helical shaped portion of the curved body.

* * * * *